United States Patent
Shim et al.

(10) Patent No.: US 9,689,019 B2
(45) Date of Patent: Jun. 27, 2017

(54) BIOMARKER FOR DIAGNOSING TOXICITY OF NANOPARTICLES AND METHOD FOR EVALUATING TOXICITY OF NANOPARTICLES USING THE SAME

(71) Applicant: AJOU UNIVERSITY INDUSTRY-ACADEMIC COOPERATION FOUNDATION, Suwon-si, Gyeonggi-do (KR)

(72) Inventors: Woo Young Shim, Suwon-si (KR); Duc Toan Nguyen, Hanoi (VE); Gwang Lee, Suwon-si (KR); Man Jeong Paik, Seoul (KR); Jae Ho Kim, Seongnam-si (KR); Sang Mi Hyun, Seoul (KR); Ki Ryung Choi, Seoul (KR); Sung Su Park, Seoul (KR); Jin Seok Kang, Seongnam-si (KR); Jeom Soon Shim, Seoul (KR); Tae-Hwan Shin, Daegu (KR); Geetika Phukan, Suwon-si (KR)

(73) Assignee: AJOU UNIVERSITY INDUSTRY-ACADEMIC COOPERATION FOUNDATION, Suwon-si, Gyeonggi-Do (KR)

( * ) Notice: Subject to any disclaimer, the term of this patent is extended or adjusted under 35 U.S.C. 154(b) by 380 days.

(21) Appl. No.: 13/760,450

(22) Filed: Feb. 6, 2013

(65) Prior Publication Data
US 2014/0024545 A1     Jan. 23, 2014

(30) Foreign Application Priority Data

Jul. 23, 2012    (KR) ........................ 10-2012-0080203
Jul. 23, 2012    (KR) ........................ 10-2012-0080204

(51) Int. Cl.
    *C12Q 1/68*       (2006.01)
    *C12Q 1/02*       (2006.01)
    *G01N 33/50*     (2006.01)

(52) U.S. Cl.
    CPC ........... *C12Q 1/025* (2013.01); *C12Q 1/6809* (2013.01); *C12Q 1/6876* (2013.01); *C12Q 1/6883* (2013.01); *G01N 33/5091* (2013.01); *C12Q 2600/142* (2013.01); *C12Q 2600/158* (2013.01); *G01N 2800/40* (2013.01); *G01N 2800/60* (2013.01)

(58) Field of Classification Search
CPC   C12Q 1/025; C12Q 1/6809; C12Q 2600/142; G01N 33/5091
See application file for complete search history.

(56) References Cited

FOREIGN PATENT DOCUMENTS

KR    10-2007-0069317      7/2007

OTHER PUBLICATIONS

Kares et al 2010 Kidney International 78: 96-102.*
*Homo sapiens* aldehyde dehydrogenase 1 family, member A2 (ALDH1A2), transcript variant 1, mRNA. Datasheet, [online]. National Center for Biotechnology Information. Retrieved on Apr. 2, 2014. Retrieved from the Internet: <http://www.ncbi.nlm.nih.gov/nuccore/332634689>.*
Yildirimer et al 2011 Nano Today 6: 585-607.*
Shim et al 2012 ACS Nano 6: 7665-7680; epub Jul. 24, 2012.*
Enard et al. (Science 2002 vol. 296 p. 340).*
Cobb et al (Crit Care Med 2002 vol. 30 p. 2711).*
Cheung et al (Nature Genetics 2003 vol. 33 p. 422).*
Dermer et al. (Biotechnology vol. 12, Mar. 1994, p. 320).*

* cited by examiner

*Primary Examiner* — Katherine Salmon
(74) *Attorney, Agent, or Firm* — Revolution IP, PLLC

(57) ABSTRACT

Disclosed is a biomarker composition for diagnosing the toxicity of nanoparticles, which shows a change in expression by exposure to the nanoparticles, the biomarker composition comprising at least one gene selected from the group consisting of aldehyde dehydrogenase, glutamic-pyruvate transaminase, glutamate dehydrogenase, glutami-coxaloacetic transaminase, glutamic acid decarboxylase and glutamate-ammonia ligase, and to a method for evaluating the toxicity of nanoparticles using the same. The biomarker is a gene marker having a high correlation with the toxicity of nanoparticles, and the use of the biomarker can determine whether nanoparticles have toxicity, with high detection sensitivity. Also, the method is useful in monitoring or evaluating the toxicity of nanoparticles by analyzing factors having a high correlation with toxicity of nanoparticles. Furthermore, the method can be effectively used as a tool for studying various diseases caused by exposure to nanoparticles or evaluating the effects of nanoparticles on health.

6 Claims, 12 Drawing Sheets

BIOMARKER FOR DIAGNOSING TOXICITY OF NANOPARTICLES AND METHOD FOR EVALUATING TOXICITY OF NANOPARTICLES USING THE SAME

CROSS REFERENCE TO PRIOR APPLICATION

The present application claims priority under 35 U.S.C. §119 to Korean Patent Application Nos. 10-2012-0080203 (filed on Jul. 23, 2012) and 10-2012-0080204 (filed on Jul. 23, 2012), which are hereby incorporated by reference in their entirety.

BACKGROUND OF THE INVENTION

Field of the Invention

The present invention relates to a biomarker for diagnosing the toxicity of nanoparticles, a microarray chip for diagnosing the toxicity of nanoparticles, which comprises the same, and a method for evaluating the toxicity of nanoparticles using the same.

Description of the Prior Art

With the development of nanotechnology, nanomaterials have been used in various applications, including industrial, medical and research applications. Thus, not only workers who produce nanomaterials, but also general persons have been frequently exposed to and come in contact with nanomaterials.

Nanotechnology provides many advantages and benefits such that it is recognized as a new technological revolution in the whole industry, whereas it is well known to have a potential risk. This potential risk appears to be attributable to the characteristics of nanotechnology.

In other words, smaller particles have larger specific surface areas, and these particles smaller particles have increased toxicity when they react with biological tissue. It has been proven through scientific experiments that the toxicity of several kinds of particles, such as titanium dioxide powder, carbon powder and diesel particles, increases to cause inflammation, as the size of the particles decreases. In addition, it was reported that ultrafine nanoparticles can penetrate deeply into the alveolus through the airway or the mucous or migrate to the brain. Additionally, several recent studies report that the in vivo accumulation of nanoparticles causes disease or a disorder of the central nervous system. Thus, in recent years, with the development of nanotechnology, the evaluation of safety of nanotechnology has been actively performed. With respect to this evaluation, studies have been concentrated mainly on devices for evaluating the toxicity of nanoparticles (Korean Patent Registration No. 10-0798149). In addition, a clear methodological guide or biological marker allowing the evaluation of safety of various nanomaterials has not yet been standardized.

SUMMARY OF THE INVENTION

Therefore, it is an object of the present invention to provide a biological marker for evaluating the safety of nanomaterials by evaluating the functional changes of metabolites and genes using an approach based on systems biological analysis.

To achieve the above object, the present invention provides a biomarker composition for diagnosing the toxicity of nanoparticles, which shows a change in expression by exposure to the nanoparticles, the biomarker composition comprising at least one gene selected from the group consisting of Genebank NM_000689.4 (ALDH1A1, aldehyde dehydrogenase 1 family member A1), Genebank NM_003888.3 (ALDH1A2, aldehyde dehydrogenase 1 family member A2, transcript variant 1), Genebank NM_170696.2 (ALDH1A2, aldehyde dehydrogenase 1 family member A2, transcript variant 2), Genebank NM_170697.2 (ALDH1A2, aldehyde dehydrogenase 1 family member A2, transcript variant 3), Genebank NM_001206897.1 (ALDH1A2, aldehyde dehydrogenase 1 family member A2, transcript variant 4), Genebank NM_000693.2 (ALDH1A3, aldehyde dehydrogenase 1 family member A3), Genebank NM_000692.4 (ALDH1B1, aldehyde dehydrogenase 1 family member B1), Genebank NM_001270364.1 (ALDH1L1, aldehyde dehydrogenase 1 family member L1, transcript variant 1), Genebank NM_012190.3 (ALDH1L1, aldehyde dehydrogenase 1 family member L1, transcript variant 2), Genebank NM_001270365.1 (ALDH1L1, aldehyde dehydrogenase 1 family member L1, transcript variant 3), Genebank NR_072979.1 (ALDH1L1, aldehyde dehydrogenase 1 family member L1, transcript variant 4), Genebank NM_001034173.3 (ALDH1L2, aldehyde dehydrogenase 1 family member L2), Genebank NM_000690.3 (ALDH2, aldehyde dehydrogenase 2, transcript variant 1), Genebank NM_001204889.1 (ALDH2, aldehyde dehydrogenase 2, transcript variant 2), Genebank NM_001135168.1 (ALDH3A1, aldehyde dehydrogenase 3 family member A1, transcript variant 1), Genebank NM_000691.4 (ALDH3A1, aldehyde dehydrogenase 3 family member A1, transcript variant 2), Genebank NM_001135167.1 (ALDH3A1, aldehyde dehydrogenase 3 family member A1, transcript variant 3), Genebank NM_001031806.1 (ALDH3A2, aldehyde dehydrogenase 3 family member A2, transcript variant 1), Genebank NM_000382.2 (ALDH3A2, aldehyde dehydrogenase 3 family member A2, transcript variant 2), Genebank NM_000694.2 (ALDH3B1, aldehyde dehydrogenase 3 family member B1, transcript variant 1), Genebank NM_001030010.1 (ALDH3B1, aldehyde dehydrogenase 3 family member B1, transcript variant 2), Genebank NM_001161473.1 (ALDH3B1, aldehyde dehydrogenase 3 family member B1, transcript variant 3), Genebank NM_000695.3 (ALDH3B2, aldehyde dehydrogenase 3 family member B2, transcript variant 1), Genebank NM_001031615.1 (ALDH3B2, aldehyde dehydrogenase 3 family member B2, transcript variant 2), Genebank NM_001161504.1 (ALDH4A1, aldehyde dehydrogenase 4 family member A1), Genebank NM_170740.1 (ALDH5A1, aldehyde dehydrogenase 5 family member A1, transcript variant 1), Genebank NM_001080.3 (ALDH5A1, aldehyde dehydrogenase 5 family member A1, transcript variant 2), Genebank NM_005589.2 (ALDH6A1, aldehyde dehydrogenase 6 family member A1), Genebank NM_001201377.1 (ALDH7A1, aldehyde dehydrogenase 7 family member A1, transcript variant 1), Genebank NM_001202404.1 (ALDH7A1, aldehyde dehydrogenase 7 family member A1, transcript variant 2), Genebank NM_022568.3 (ALDH8A1, aldehyde dehydrogenase 8 family member A1, transcript variant 1), Genebank NM_170771.2 (ALDH8A1, aldehyde dehydrogenase 8 family member A1, transcript variant 2), Genebank NM_001193480.1 (ALDH8A1, aldehyde dehydrogenase 8 family member A1, transcript variant 3), Genebank NM_000696.3 (ALDH9A1, aldehyde dehydrogenase 9 family member A1), Genebank NM_153329.3 (ALDH16A1, aldehyde dehydrogenase 16 family member A1, transcript variant 1), Genebank NM_001145396.1 (ALDH16A1, aldehyde dehydrogenase 16 family member A1, transcript variant 2), Genebank NM_002860.3

(ALDH18A1, aldehyde dehydrogenase 18 family member A1, transcript variant 1), Genebank NM_001017423.1 (ALDH18A1, aldehyde dehydrogenase 18 family member A1, transcript variant 2), Genebank NM_005309.2 (GPT1, glutamic-pyruvate transaminase 1), Genebank NM_133443.2 (GPT2, glutamic-pyruvate transaminase 2, transcript variant 1), Genebank NM_001142466.1 (GPT2, glutamic-pyruvate transaminase 2, transcript variant 2), Genebank NM_005271.3 (GLUD1, glutamate dehydrogenase 1), Genebank NM_012084.3 (GLUD2, glutamate dehydrogenase 2), Genebank NM_002079.2 (GOT1, glutamicoxaloacetic transaminase 1), Genebank NM_002080.2 (GOT2, glutamicoxaloacetic transaminase 2), Genebank NM_013445.3 (GAD1, glutamic acid decarboxylase 1, transcript variant GAD25), Genebank NM_000817.2 (GAD1, glutamic acid decarboxylase 1, transcript variant GAD67), Genebank NM_000818.2 (GAD2, glutamic acid decarboxylase 2, transcript variant 1), Genebank NM_001134366.1 (GAD2, glutamic acid decarboxylase 2, transcript variant 2), Genebank NM_002065.5 (GLUL, glutamate-ammonia ligase, transcript variant 1), Genebank NM_001033044.2 (GLUL, glutamate-ammonia ligase, transcript variant 2), and Genebank NM_001033056.2 (GLUL, glutamateammonia ligase, transcript variant 3).

The present invention also provides a microarray chip for diagnosing the toxicity of nanoparticles, wherein the microarray chip is integrated with: the entire nucleic acid sequence of at least one gene selected from the above-described biomarker genes; or an oligonucleotide that is a fragment of the gene; or a complementary strand molecule thereof.

The present invention also provides a kit for diagnosing the toxicity of nanoparticles, which comprises said microarray chip.

The present invention also provides a method for evaluating the toxicity of nanoparticles, the method comprising the steps of:

obtaining a tissue or cell sample from a mammal exposed to the nanoparticles;

analyzing the expression of a gene in the sample, the gene being at least one selected from the group consisting of Genebank NM_000689.4 (ALDH1A1, aldehyde dehydrogenase 1 family member A1), Genebank NM_003888.3 (ALDH1A2, aldehyde dehydrogenase 1 family member A2, transcript variant 1), Genebank) NM_170696.2 (ALDH1A2, aldehyde dehydrogenase 1 family member A2, transcript variant 2), Genebank NM_170697.2 (ALDH1A2, aldehyde dehydrogenase 1 family member A2, transcript variant 3), Genebank NM_001206897.1 (ALDH1A2, aldehyde dehydrogenase 1 family member A2, transcript variant 4), Genebank NM_000693.2 (ALDH1A3, aldehyde dehydrogenase 1 family member A3), Genebank NM_000692.4 (ALDH1B1, aldehyde dehydrogenase 1 family member B1), Genebank NM_001270364.1 (ALDH1L1, aldehyde dehydrogenase 1 family member L1, transcript variant 1), Genebank NM_012190.3 (ALDH1L1, aldehyde dehydrogenase 1 family member L1, transcript variant 2), Genebank NM_001270365.1 (ALDH1L1, aldehyde dehydrogenase 1 family member L1, transcript variant 3), Genebank NR_072979.1 (ALDH1L1, aldehyde dehydrogenase 1 family member L1, transcript variant 4), Genebank NM_001034173.3 (ALDH1L2, aldehyde dehydrogenase 1 family member L2), Genebank NM_000690.3 (ALDH2, aldehyde dehydrogenase 2, transcript variant 1), Genebank NM_001204889.1 (ALDH2, aldehyde dehydrogenase 2, transcript variant 2), Genebank NM_001135168.1 (ALDH3A1, aldehyde dehydrogenase 3 family member A1, transcript variant 1), Genebank NM_000691.4 (ALDH3A1, aldehyde dehydrogenase 3 family member A1, transcript variant 2), Genebank NM_001135167.1 (ALDH3A1, aldehyde dehydrogenase 3 family member A1, transcript variant 3), Genebank NM_001031806.1 (ALDH3A2, aldehyde dehydrogenase 3 family member A2, transcript variant 1), Genebank NM_000382.2 (ALDH3A2, aldehyde dehydrogenase 3 family member A2, transcript variant 2), Genebank NM_000694.2 (ALDH3B1, aldehyde dehydrogenase 3 family member B1, transcript variant 1), Genebank NM_001030010.1 (ALDH3B1, aldehyde dehydrogenase 3 family member B1, transcript variant 2), Genebank NM_001161473.1 (ALDH3B1, aldehyde dehydrogenase 3 family member B1, transcript variant 3), Genebank NM_000695.3 (ALDH3B2, aldehyde dehydrogenase 3 family member B2, transcript variant 1), Genebank NM_001031615.1 (ALDH3B2, aldehyde dehydrogenase 3 family member B2, transcript variant 2), Genebank) NM_001161504.1 (ALDH4A1, aldehyde dehydrogenase 4 family member A1), Genebank NM_170740.1 (ALDH5A1, aldehyde dehydrogenase 5 family member A1, transcript variant 1), Genebank NM_001080.3 (ALDH5A1, aldehyde dehydrogenase 5 family member A1, transcript variant 2), Genebank NM_005589.2 (ALDH6A1, aldehyde dehydrogenase 6 family member A1), Genebank NM_001201377.1 (ALDH7A1, aldehyde dehydrogenase 7 family member A1, transcript variant 1), Genebank NM_001202404.1 (ALDH7A1, aldehyde dehydrogenase 7 family member A1, transcript variant 2), Genebank NM_022568.3 (ALDH8A1, aldehyde dehydrogenase 8 family member A1, transcript variant 1), Genebank NM_170771.2 (ALDH8A1, aldehyde dehydrogenase 8 family member A1, transcript variant 2), Genebank NM_001193480.1 (ALDH8A1, aldehyde dehydrogenase 8 family member A1, transcript variant 3), Genebank NM_000696.3 (ALDH9A1, aldehyde dehydrogenase 9 family member A1), Genebank NM_153329.3 (ALDH16A1, aldehyde dehydrogenase 16 family member A1, transcript variant 1), Genebank NM_001145396.1 (ALDH16A1, aldehyde dehydrogenase 16 family member A1, transcript variant 2), Genebank NM_002860.3 (ALDH18A1, aldehyde dehydrogenase 18 family member A1, transcript variant 1), Genebank NM_001017423.1 (ALDH18A1, aldehyde dehydrogenase 18 family member A1, transcript variant 2), Genebank NM_005309.2 (GPT1, glutamic-pyruvate transaminase 1), Genebank NM_133443.2 (GPT2, glutamic-pyruvate transaminase 2, transcript variant 1), Genebank NM_001142466.1 (GPT2, glutamic-pyruvate transaminase 2, transcript variant 2), Genebank NM_005271.3 (GLUD1, glutamate dehydrogenase 1), Genebank NM_012084.3 (GLUD2, glutamate dehydrogenase 2), Genebank NM_002079.2 (GOT1, glutamicoxaloacetic transaminase 1), Genebank NM_002080.2 (GOT2, glutamicoxaloacetic transaminase 2), Genebank NM_013445.3 (GAD1, glutamic acid decarboxylase 1, transcript variant GAD25), Genebank NM_000817.2 (GAD1, glutamic acid decarboxylase 1, transcript variant GAD67), Genebank NM_000818.2 (GAD2, glutamic acid decarboxylase 2, transcript variant 1), Genebank NM_001134366.1 (GAD2, glutamic acid decarboxylase 2, transcript variant 2), Genebank NM_002065.5 (GLUL, glutamate-ammonia ligase, transcript variant 1), Genebank NM_001033044.2 (GLUL, glutamate-ammonia ligase, transcript variant 2), and Genebank NM_001033056.2 (GLUL, glutamateammonia ligase, transcript variant 3); and comparing the expression level of the gene to that of a control group.

The method for evaluating the toxicity of nanoparticles may further comprise the steps of: analyzing at least one selected from the group consisting of ROS content, ATP content, intracellular mitochondrial damage, a change in intracellular mitochondrial membrane potential, glutamic acid content, and pyruvate content; and comparing the analysis result with that of the control group.

The present invention also provides a method for evaluating the toxicity of nanoparticles, the method comprising the steps of:

obtaining a tissue or cell sample from mammal exposed to the nanoparticles;

analyzing the sample for at least one selected from the group consisting of reactive oxygen content (ROS) content, ATP content, intracellular mitochondrial damage, a change in intracellular mitochondrial membrane potential, glutamic acid content, and pyruvate content; and comparing the analysis result with that of a control group.

DETAILED DESCRIPTION OF THE INVENTION

Figure 1:
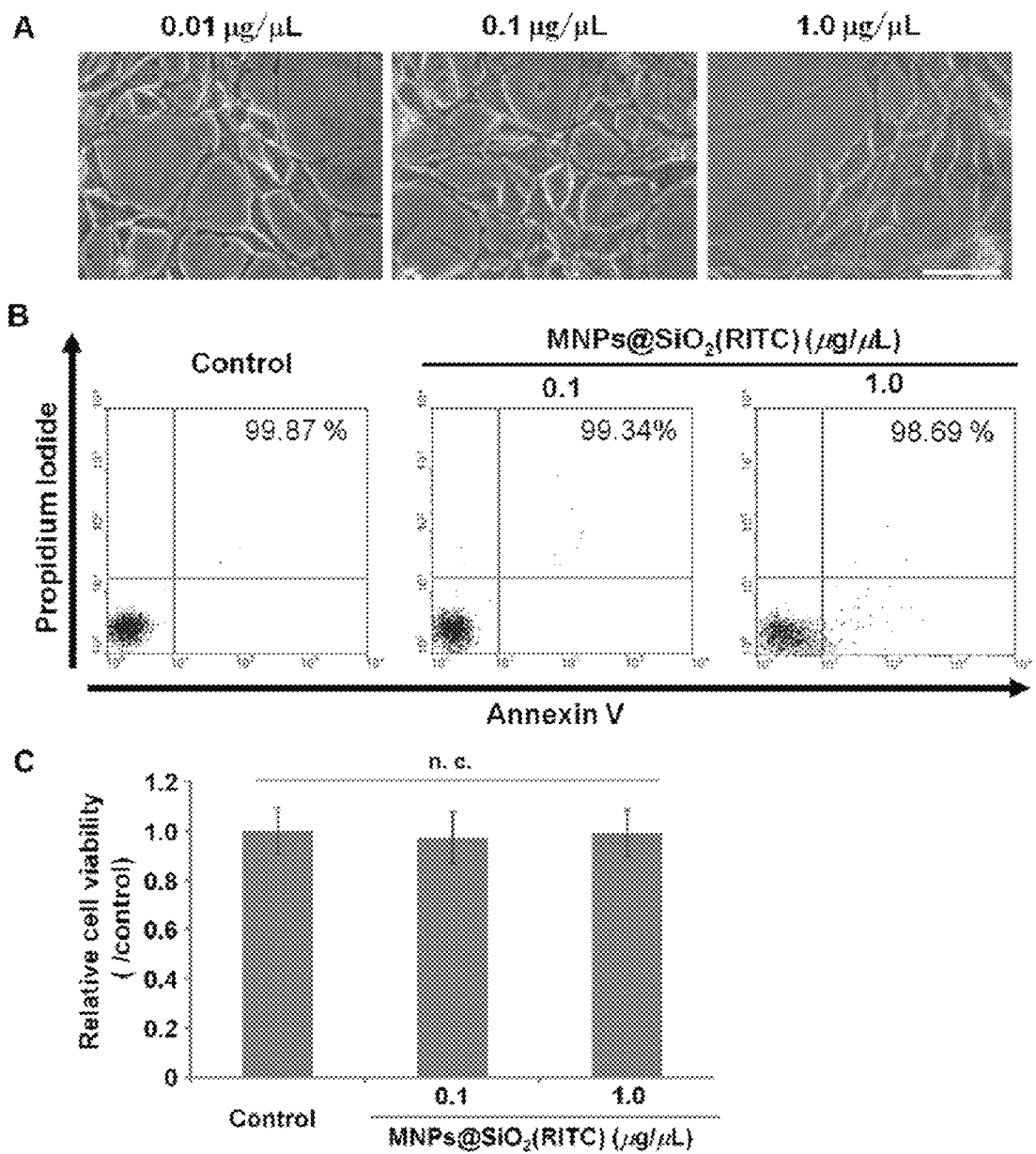
FIG. 1 shows the results of analyzing the cytotoxicity of MNPs@SiO$_2$(RITC) in Example 1.

The present invention provides a biomarker composition for diagnosing the toxicity of nanoparticles, which shows a change in expression by exposure to the nanoparticles, the biomarker composition comprising at least one gene selected from the group consisting of Genebank NM_000689.4 (ALDH1A1, aldehyde dehydrogenase 1 family member A1), Genebank NM_003888.3 (ALDH1A2, aldehyde dehydrogenase 1 family member A2, transcript variant 1), Genebank NM_170696.2 (ALDH1A2, aldehyde dehydrogenase 1 family member A2, transcript variant 2), Genebank NM_170697.2 (ALDH1A2, aldehyde dehydrogenase 1 family member A2, transcript variant 3), Genebank NM_001206897.1 (ALDH1A2, aldehyde dehydrogenase 1 family member A2, transcript variant 4), Genebank NM_000693.2 (ALDH1A3, aldehyde dehydrogenase 1 family member A3), Genebank NM_000692.4 (ALDH1B1, aldehyde dehydrogenase 1 family member B1), Genebank NM_001270364.1 (ALDH1L1, aldehyde dehydrogenase 1 family member L1, transcript variant 1), Genebank NM_012190.3 (ALDH1L1, aldehyde dehydrogenase 1 family member L1, transcript variant 2), Genebank NM_001270365.1 (ALDH1L1, aldehyde dehydrogenase 1 family member L1, transcript variant 3), Genebank NR_072979.1 (ALDH1L1, aldehyde dehydrogenase 1 family member L1, transcript variant 4), Genebank NM_001034173.3 (ALDH1L2, aldehyde dehydrogenase 1 family member L2), Genebank NM_000690.3 (ALDH2, aldehyde dehydrogenase 2, transcript variant 1), Genebank NM_001204889.1 (ALDH2, aldehyde dehydrogenase 2, transcript variant 2), Genebank NM_001135168.1 (ALDH3A1, aldehyde dehydrogenase 3 family member A1, transcript variant 1), Genebank NM_000691.4 (ALDH3A1, aldehyde dehydrogenase 3 family member A1, transcript variant 2), Genebank NM_001135167.1 (ALDH3A1, aldehyde dehydrogenase 3 family member A1, transcript variant 3), Genebank NM_001031806.1 (ALDH3A2, aldehyde dehydrogenase 3 family member A2, transcript variant 1), Genebank NM_000382.2 (ALDH3A2, aldehyde dehydrogenase 3 family member A2, transcript variant 2), Genebank NM_000694.2 (ALDH3B1, aldehyde dehydrogenase 3 family member B1, transcript variant 1), Genebank NM_001030010.1 (ALDH3B1, aldehyde dehydrogenase 3 family member B1, transcript variant 2), Genebank NM_001161473.1 (ALDH3B1, aldehyde dehydrogenase 3 family member B1, transcript variant 3), Genebank NM_000695.3 (ALDH3B2, aldehyde dehydrogenase 3 family member B2, transcript variant 1), Genebank NM_001031615.1 (ALDH3B2, aldehyde dehydrogenase 3 family member B2, transcript variant 2), Genebank NM_001161504.1 (ALDH4A1, aldehyde dehydrogenase 4 family member A1), Genebank NM_170740.1 (ALDH5A1, aldehyde dehydrogenase 5 family member A1, transcript variant 1), Genebank NM_001080.3 (ALDH5A1, aldehyde dehydrogenase 5 family member A1, transcript variant 2), Genebank NM_005589.2 (ALDH6A1, aldehyde dehydrogenase 6 family member A1), Genebank NM_001201377.1 (ALDH7A1, aldehyde dehydrogenase 7 family member A1, transcript variant 1), Genebank NM_001202404.1 (ALDH7A1, aldehyde dehydrogenase 7 family member A1, transcript variant 2), Genebank NM_022568.3 (ALDH8A1, aldehyde dehydrogenase 8 family member A1, transcript variant 1), Genebank NM_170771.2 (ALDH8A1, aldehyde dehydrogenase 8 family member A1, transcript variant 2), Genebank NM_001193480.1 (ALDH8A1, aldehyde dehydrogenase 8 family member A1, transcript variant 3), Genebank NM_000696.3 (ALDH9A1, aldehyde dehydrogenase 9 family member A1), Genebank NM_153329.3 (ALDH16A1, aldehyde dehydrogenase 16 family member A1, transcript variant 1), Genebank NM_001145396.1 (ALDH16A1, aldehyde dehydrogenase 16 family member A1, transcript variant 2), Genebank NM_002860.3 (ALDH18A1, aldehyde dehydrogenase 18 family member A1, transcript variant 1), Genebank NM_001017423.1 (ALDH18A1, aldehyde dehydrogenase 18 family member A1, transcript variant 2), Genebank NM_005309.2 (GPT1, glutamic-pyruvate transaminase 1), Genebank NM_133443.2 (GPT2, glutamic-pyruvate transaminase 2, transcript variant 1), Genebank NM_001142466.1 (GPT2, glutamic-pyruvate transaminase 2, transcript variant 2), Genebank NM_005271.3 (GLUD1, glutamate dehydrogenase 1), Genebank NM_012084.3 (GLUD2, glutamate dehydrogenase 2), Genebank NM_002079.2 (GOT1, glutamicoxaloacetic transaminase 1), Genebank NM_002080.2 (GOT2, glutamicoxaloacetic transaminase 2), Genebank NM_013445.3 (GAD1, glutamic acid decarboxylase 1, transcript variant GAD25), Genebank NM_000817.2 (GAD1, glutamic acid decarboxylase 1, transcript variant GAD67), Genebank NM_000818.2 (GAD2, glutamic acid decarboxylase 2, transcript variant 1), Genebank NM_001134366.1 (GAD2, glutamic acid decarboxylase 2, transcript variant 2), Genebank NM_002065.5 (GLUL, glutamate-ammonia ligase, transcript variant 1), Genebank NM_001033044.2 (GLUL, glutamate-ammonia ligase, transcript variant 2), and Genebank NM_001033056.2 (GLUL, glutamateammonia ligase, transcript variant 3).

In one embodiment of the present invention, the biomarker composition may essentially comprise at least one gene selected from the group consisting of Genebank NM_001161504.1 (ALDH4H1, aldehyde dehydrogenase 4 family member A1), Genebank NM_133443.2 (GPT2, glutamic34 pyruvate transaminase 2), Genebank NM_005271.3 (GLUD1, glutamate dehydrogenase 1), Genebank NM_002080.2 (GOT2, glutamic oxaloacetic transaminase 2), Genebank NM_013445.3 (GAD1, glutamic acid decarboxylase 1), and Genebank NM_002065.5 (GLUL, glutamate ammonia ligase).

The present inventors have conducted studies to evaluate the toxic effect of exposure to nanoparticles by the change in gene expression caused by the nanoparticles, and as a result, have found that, when cells are treated with a specific or higher concentration of nanoparticles, the expression of glutamic acid metabolism-related genes and concentration of glutamic acid in the cells are changed, and this change can be used as a marker for evaluating the toxicity of nanoparticles, thereby completing the present invention.

In one embodiment of the present invention, the nanoparticles may be any nanoparticles whose toxicity is increased upon reaction with biological tissue. More specifically, the nanoparticles include, but are not limited to, atmospheric nanoparticles, nanoparticles contained in cosmetic compositions, nanoparticles contained in pharmaceutical compositions, semiconductor nanoparticles, and the like.

The nanoparticles may have a core-shell structure wherein the shell may include silica, but the scope of the present invention is not limited thereto.

Figure 5:
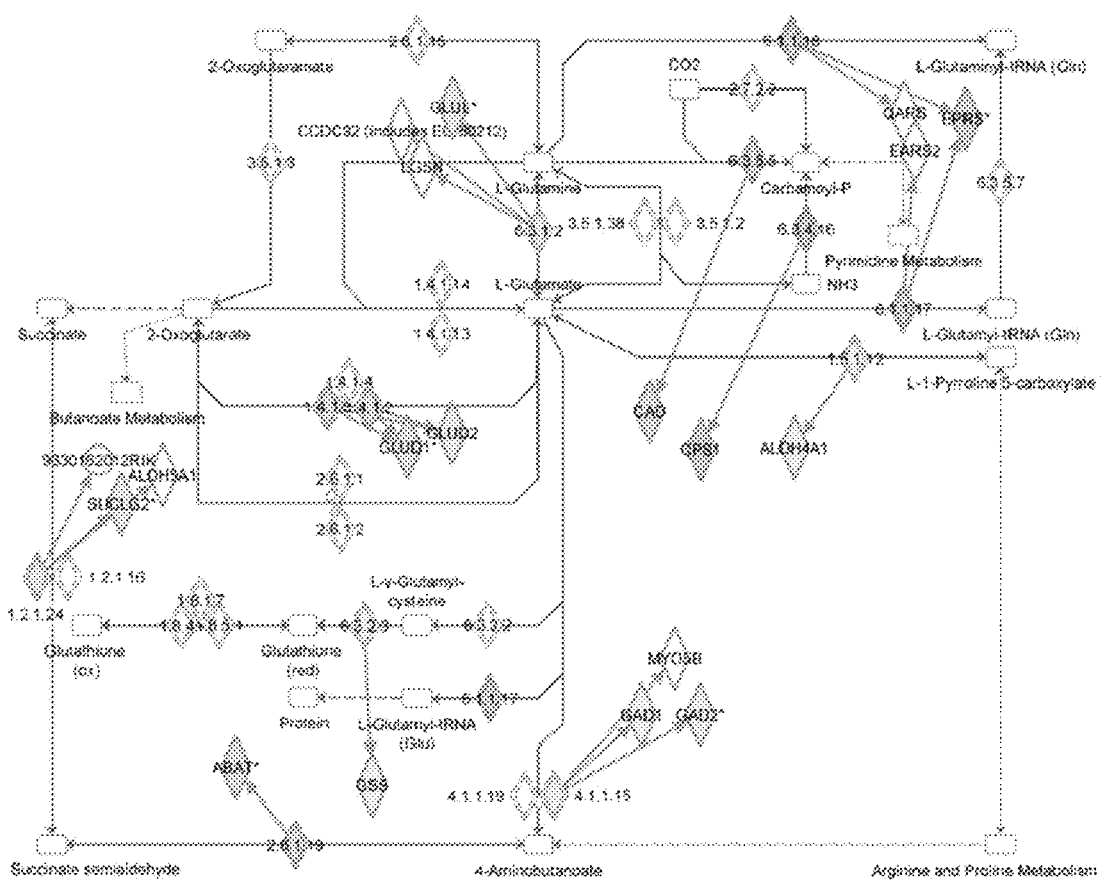
FIG. 5 is a schematic diagram of a glutamic acid metabolic pathway constructed using Ingenuity Pathway Analysis (IPA).

In one specific example, the present inventors categorized a total of 291 genes, including 205 upregulated genes and 86 downregulated genes after treatment with high concentrations of nanoparticles, and then analyzed the biological functions and typical pathways of the differentially expressed genes using Ingenuity Pathway Analysis (IPA; Ingenuity, USA). As a result, the present inventors could screen the following six genes related to the glutamic acid metabolic pathway: aldehyde dehydrogenase, glutamic-pyruvate transaminase, glutamate dehydrogenase, glutamicoxaloacetic transaminase, glutamic acid decarboxylase and glutamate-ammonia ligase genes (FIG. 5).

In one embodiment of the present invention, aldehyde dehydrogenase and glutamic-pyruvate transaminase genes are genes whose expression is increased by exposure to nanoparticles. The increased expression level of the genes is 1.25-fold or more compared to a normal expression level, and when the expression of the genes in cells is increased compared to that in a control group, the nanoparticles can be evaluated to have toxicity.

More specifically, examples of the aldehyde dehydrogenase and glutamic-pyruvate transaminase genes whose expression is increased by exposure to nanoparticles include Genebank NM_000689.4 (ALDH1A1, aldehyde dehydrogenase 1 family member A1), Genebank NM_003888.3 (ALDH1A2, aldehyde dehydrogenase 1 family member A2, transcript variant 1), Genebank NM_170696.2 (ALDH1A2, aldehyde dehydrogenase 1 family member A2, transcript variant 2), Genebank NM_170697.2 (ALDH1A2, aldehyde dehydrogenase 1 family member A2, transcript variant 3), Genebank NM_001206897.1 (ALDH1A2, aldehyde dehydrogenase 1 family member A2, transcript variant 4), Genebank NM_000693.2 (ALDH1A3, aldehyde dehydrogenase 1 family member A3), Genebank NM_000692.4 (ALDH1B1, aldehyde dehydrogenase 1 family member B1), Genebank NM_001270364.1 (ALDH1L1, aldehyde dehydrogenase 1 family member L1, transcript variant 1), Genebank) NM_012190.3 (ALDH1L1, aldehyde dehydrogenase 1 family member L1, transcript variant 2), Genebank NM_001270365.1 (ALDH1L1, aldehyde dehydrogenase 1 family member L1, transcript variant 3), Genebank NR_072979.1 (ALDH1L1, aldehyde dehydrogenase 1 family member L1, transcript variant 4), Genebank NM_001034173.3 (ALDH1L2, aldehyde dehydrogenase 1 family member L2), Genebank NM_000690.3 (ALDH2, aldehyde dehydrogenase 2, transcript variant 1), Genebank NM_001204889.1 (ALDH2, aldehyde dehydrogenase 2, transcript variant 2), Genebank NM_001135168.1 (ALDH3A1, aldehyde dehydrogenase 3 family member A1, transcript variant 1), Genebank NM_000691.4 (ALDH3A1, aldehyde dehydrogenase 3 family member A1, transcript variant 2), Genebank NM_001135167.1 (ALDH3A1, aldehyde dehydrogenase 3 family member A1, transcript variant 3), Genebank NM_001031806.1 (ALDH3A2, aldehyde dehydrogenase 3 family member A2, transcript variant 1), Genebank NM_000382.2 (ALDH3A2, aldehyde dehydrogenase 3 family member A2, transcript variant 2), Genebank NM_000694.2 (ALDH3B1, aldehyde dehydrogenase 3 family member B1, transcript variant 1), Genebank NM_001030010.1 (ALDH3B1, aldehyde dehydrogenase 3 family member B1, transcript variant 2), Genebank NM_001161473.1 (ALDH3B1, aldehyde dehydrogenase 3 family member B1, transcript variant 3), Genebank NM_000695.3 (ALDH3B2, aldehyde dehydrogenase 3 family member B2, transcript variant 1), Genebank NM_001031615.1 (ALDH3B2, aldehyde dehydrogenase 3 family member B2, transcript variant 2), Genebank NM_001161504.1 (ALDH4A1, aldehyde dehydrogenase 4 family member A1), Genebank NM_170740.1 (ALDH5A1, aldehyde dehydrogenase 5 family member A1, transcript variant 1), Genebank NM_001080.3 (ALDH5A1, aldehyde dehydrogenase 5 family member A1, transcript variant 2), Genebank NM_005589.2 (ALDH6A1, aldehyde dehydrogenase 6 family member A1), Genebank NM_001201377.1 (ALDH7A1, aldehyde dehydrogenase 7 family member A1, transcript variant 1), Genebank NM_001202404.1 (ALDH7A1, aldehyde dehydrogenase 7 family member A1, transcript variant 2), Genebank NM_022568.3 (ALDH8A1, aldehyde dehydrogenase 8 family member A1, transcript variant 1), Genebank NM_170771.2 (ALDH8A1, aldehyde dehydrogenase 8 family member A1, transcript variant 2), Genebank NM_001193480.1 (ALDH8A1, aldehyde dehydrogenase 8 family member A1, transcript variant 3), Genebank NM_000696.3 (ALDH9A1, aldehyde dehydrogenase 9 family member A1), Genebank NM_153329.3 (ALDH16A1, aldehyde dehydrogenase 16 family member A1, transcript variant 1), Genebank NM_001145396.1 (ALDH16A1, aldehyde dehydrogenase 16 family member A1, transcript variant 2), Genebank NM_002860.3 (ALDH18A1, aldehyde dehydrogenase 18 family member A1, transcript variant 1), Genebank NM_001017423.1 (ALDH18A1, aldehyde dehydrogenase 18 family member A1, transcript variant 2), Genebank NM_005309.2 (GPT1, glutamic pyruvate transaminase 1), Genebank NM_133443.2 (GPT2, glutamic-pyruvate transaminase 2, transcript variant 1) and Genebank NM_001142466.1 (GPT2, glutamic-pyruvate transaminase 2, transcript variant 2).

In another embodiment of the present invention, glutamate dehydrogenase, glutamicoxaloacetic transaminase, glutamic acid decarboxylase and glutamate-ammonia ligase genes are genes whose expression is decreased by exposure to nanoparticles. The decreased expression level of the genes is 0.75-fold or less compared to a normal expression level, and when the expression of the genes in cells is decreased compared to that in a control group, the nanoparticles can be evaluated to have toxicity.

More specifically, examples of the glutamate dehydrogenase, glutamicoxaloacetic transaminase, glutamic acid decarboxylase and glutamate-ammonia ligase genes whose expression is decreased by exposure to nanoparticles include Genebank NM_005271.3 (GLUD1, glutamate dehydrogenase 1), Genebank NM_012084.3 (GLUD2, glutamate dehydrogenase 2), Genebank NM_002079.2 (GOT1, glutamicoxaloacetic transaminase 1), Genebank NM_002080.2 (GOT2, glutamicoxaloacetic transaminase 2), Genebank NM_013445.3 (GAD1, glutamic acid decarboxylase 1, transcript variant GAD25), Genebank NM_000817.2 (GAD1, glutamic acid decarboxylase 1, transcript variant GAD67), Genebank NM_000818.2 (GAD2, glutamic acid decarboxylase 2, transcript variant 1), Genebank NM_001134366.1 (GAD2, glutamic acid decarboxylase 2, transcript variant 2), Genebank NM_002065.5 (GLUL, glutamate-ammonia ligase, transcript variant 1), Genebank NM_001033044.2 (GLUL, glutamate-ammonia ligase, transcript variant 2) and Genebank NM_001033056.2 (GLUL, glutamateammonia ligase, transcript variant 3).

The present invention also provides a microarray chip for diagnosing the toxicity of nanoparticles, wherein the microarray chip is integrated with: the entire nucleic acid sequence of at least one gene selected from the above-described biomarker genes; or an oligonucleotide that is a fragment of the gene; or a complementary strand molecule thereof.

In one embodiment of the present invention, the oligonucleotide or a complementary strand molecule thereof may comprise 15-50 nucleic acids of the biomarker gene.

The microarray chip for diagnosing the toxicity of nanoparticles according to the present invention can be fabricated by any method known to those skilled in the art. The method for fabricating the microarray chip is as follows. For example, the gene biomarker is preferably immobilized on a substrate for the DNA microarray chip using a piezoelectric micropipetting method or a pin-shaped spotter, but is not limited thereto. The substrate of the DNA microarray chip is preferably coated with a functional group selected from the group consisting of amino-silane, poly-L-lysine and aldehyde, but is not limited thereto. In addition, the substrate may be made of a material selected from the group consisting of slide glass, a plastic material, a metal, silicon, a nylon film and a nitrocellulose film, but is not limited thereto.

The present invention also provides a kit for diagnosing the toxicity of nanoparticles, which comprises said microarray chip.

The kit according to the present invention may further comprise a fluorescent substance. The fluorescent substance is preferably selected from the group consisting of a strepavidin-like phosphatase conjugate, a chemifluorescent substance and chemiluminescent substance, but is not limited thereto.

In addition, the kit may further comprise a reaction reagent. The reaction reagent is selected from the group consisting of hybridization buffer, reverse transcriptase for the synthesis of cDNA from mRNA, cNTPs and rNTP (pre-mixed or separated), marker reagent such as chemical inducer of fluorescent staining, and washing buffer, but is not limited thereto. In addition, any reaction reagent necessary for hybridization of the DNA microarray chip, known to those in the art, can be included in the kit.

The present invention also provides a kit for diagnosing the toxicity of nanoparticles, which comprises a primer pair complementary to the biomarker gene and capable of amplifying the biomarker gene.

The primer pair may be a pair of 15 to 50-mer forward and reverse primers designed such that an amplification product of the biomarker gene is 100 to 300 bp in length. In addition, the kit may further comprise a reaction reagent. The reaction reagent is selected from the group consisting of hybridization buffer, reverse transcriptase for the synthesis of cDNA from mRNA, cNTPs and rNTP (pre-mixed or separated), marker reagent such as chemical inducer of fluorescent staining, and washing buffer, but is not limited thereto. In addition, any reaction reagent necessary for RT-PCR, known to those in the art, can be included in the kit.

The present invention also provides a method for evaluating the toxicity of nanoparticles, which comprises the steps of:

obtaining a tissue or cell sample from a mammal exposed to nanoparticles;

analyzing the expression of a gene in the sample, the gene being at least one selected from the group consisting of Genebank NM_000689.4 (ALDH1A1, aldehyde dehydrogenase 1 family member A1), Genebank NM_003888.3 (ALDH1A2, aldehyde dehydrogenase 1 family member A2, transcript variant 1), Genebank) NM_170696.2 (ALDH1A2, aldehyde dehydrogenase 1 family member A2, transcript variant 2), Genebank NM_170697.2 (ALDH1A2, aldehyde dehydrogenase 1 family member A2, transcript variant 3), Genebank NM_001206897.1 (ALDH1A2, aldehyde dehydrogenase 1 family member A2, transcript variant 4), Genebank NM_000693.2 (ALDH1A3, aldehyde dehydrogenase 1 family member A3), Genebank NM_000692.4 (ALDH1B1, aldehyde dehydrogenase 1 family member B1), Genebank NM_001270364.1 (ALDH1L1, aldehyde dehydrogenase 1 family member L1, transcript variant 1), Genebank NM_012190.3 (ALDH1L1, aldehyde dehydrogenase 1 family member L1, transcript variant 2), Genebank NM_001270365.1 (ALDH1L1, aldehyde dehydrogenase 1 family member L1, transcript variant 3), Genebank NR_072979.1 (ALDH1L1, aldehyde dehydrogenase 1 family member L1, transcript variant 4), Genebank NM_001034173.3 (ALDH1L2, aldehyde dehydrogenase 1 family member L2), Genebank NM_000690.3 (ALDH2, aldehyde dehydrogenase 2, transcript variant 1), Genebank NM_001204889.1 (ALDH2, aldehyde dehydrogenase 2, transcript variant 2), Genebank NM_001135168.1 (ALDH3A1, aldehyde dehydrogenase 3 family member A1, transcript variant 1), Genebank NM_000691.4 (ALDH3A1, aldehyde dehydrogenase 3 family member A1, transcript variant 2), Genebank NM_001135167.1 (ALDH3A1, aldehyde dehydrogenase 3 family member A1, transcript variant 3), Genebank NM_001031806.1 (ALDH3A2, aldehyde dehydrogenase 3 family member A2, transcript variant 1), Genebank NM_000382.2 (ALDH3A2, aldehyde dehydrogenase 3 family member A2, transcript variant 2), Genebank NM_000694.2 (ALDH3B1, aldehyde dehydrogenase 3 family member B1, transcript variant 1), Genebank NM_001030010.1 (ALDH3B1, aldehyde dehydrogenase 3 family member B1, transcript variant 2), Genebank NM_001161473.1 (ALDH3B1, aldehyde dehydrogenase 3 family member B1, transcript variant 3), Genebank NM_000695.3 (ALDH3B2, aldehyde dehydrogenase 3 family member B2, transcript variant 1), Genebank NM_001031615.1 (ALDH3B2, aldehyde dehydrogenase 3 family member B2, transcript variant 2), Genebank) NM_001161504.1 (ALDH4A1, aldehyde dehydrogenase 4 family member A1), Genebank NM_170740.1 (ALDH5A1, aldehyde dehydrogenase 5 family member A1, transcript variant 1), Genebank NM_001080.3 (ALDH5A1, aldehyde dehydrogenase 5 family member A1, transcript variant 2), Genebank NM_005589.2 (ALDH6A1, aldehyde dehydrogenase 6 family member A1), Genebank NM_001201377.1 (ALDH7A1, aldehyde dehydrogenase 7 family member A1, transcript variant 1), Genebank NM_001202404.1 (ALDH7A1, aldehyde dehydrogenase 7 family member A1, transcript variant 2), Genebank NM_022568.3 (ALDH8A1, aldehyde dehydrogenase 8 family member A1, transcript variant 1), Genebank NM_170771.2 (ALDH8A1, aldehyde dehydrogenase 8 family member A1, transcript variant 2), Genebank NM_001193480.1 (ALDH8A1, aldehyde dehydrogenase 8 family member A1, transcript variant 3), Genebank NM_000696.3 (ALDH9A1, aldehyde dehydrogenase 9 family member A1), Genebank NM_153329.3 (ALDH16A1, aldehyde dehydrogenase 16 family member A1, transcript variant 1), Genebank NM_001145396.1 (ALDH16A1, aldehyde dehydrogenase 16 family member A1, transcript variant 2), Genebank NM_002860.3 (ALDH18A1, aldehyde dehydrogenase 18 family member A1, transcript variant 1), Genebank NM_001017423.1 (ALDH18A1, aldehyde dehydrogenase 18 family member A1, transcript variant 2), Genebank NM_005309.2 (GPT1, glutamic-pyruvate transaminase 1), Genebank NM_133443.2 (GPT2, glutamic-pyruvate transaminase 2, transcript variant 1), Genebank NM_001142466.1 (GPT2, glutamic-pyruvate transaminase 2, transcript variant 2), Genebank NM_005271.3 (GLUD1, glutamate dehydrogenase 1), Genebank NM_012084.3 (GLUD2, glutamate dehydrogenase 2), Genebank NM_002079.2 (GOT1, glutamicoxaloacetic transaminase 1), Genebank NM_002080.2 (GOT2, glutamicoxaloacetic transaminase 2), Genebank NM_013445.3 (GAD1, glutamic acid decarboxylase 1, transcript variant GAD25), Genebank NM_000817.2 (GAD1, glutamic acid decarboxylase 1, transcript variant GAD67), Genebank NM_000818.2 (GAD2, glutamic acid decarboxylase 2, transcript variant 1), Genebank NM_001134366.1 (GAD2, glutamic acid decarboxylase 2, transcript variant 2), Genebank NM_002065.5 (GLUL, glutamate-ammonia ligase, transcript variant 1), Genebank NM_001033044.2 (GLUL, glutamate-ammonia ligase, transcript variant 2), and Genebank NM_001033056.2 (GLUL, glutamateammonia ligase, transcript variant 3); and comparing the expression level of the gene to that of a control group.

In one embodiment of the present invention, the toxicity of nanoparticles can be evaluated by: 1) isolating RNA from a tissue or cell sample from a mammal exposed to nanoparticles to obtain RNA of an experimental group; 2) synthesizing cDNA from each of the RNA of the experimental group and an RNA of a control group and labeling the synthesized cDNAs with different fluorescent substances; 3) hybridizing the labeled cDNAs of step 2) with the microarray chip of the present invention; 4) analyzing the microarray chip that reacted in step 3); comparing the expression of the marker gene of the experimental group with that of the control group on the basis of data obtained in step 4).

In another embodiment of the present invention, the toxicity of nanoparticles can be evaluated by: 1) isolating RNA from a tissue or cell sample from a mammal exposed to nanoparticles to obtain RNA of an experimental group; 2) subjecting each of the RNA of the experimental group and an RNA of a control group to RT-PCR (real-time reverse transcript polymerase chain reaction) using a primer pair which is complementary to the biomarker gene of the present invention and is capable of amplifying the biomarker gene; and 3) comparing the amount of the amplified gene product of step 2) with that of the control group.

More specifically, when the expression of aldehyde dehydrogenase or glutamic-pyruvate transaminase gene is increased, the nanoparticles can be evaluated to have toxicity. On the other hand, when the expression of glutamate dehydrogenase, glutamicoxaloacetic transaminase, glutamic acid decarboxylase or glutamate-ammonia ligase gene is decreased, the nanoparticles can be evaluated to have toxicity.

In still another embodiment of the present invention, the method for evaluating the toxicity of nanoparticles may further comprise the steps of: analyzing at least one selected from the group consisting of ROS (reactive oxygen species) content, ATP content, intracellular mitochondrial damage, a change in intracellular mitochondrial membrane potential, glutamic acid content, and pyruvate content; and comparing the analysis result with that of the control group.

As can be seen in the Examples below, the present inventors found that a tissue or cell sample from a mammal exposed to nanoparticles shows increased ROS content, decreased ATP content, damaged intracellular mitochondrial inner membrane, changed intracellular mitochondrial membrane potential, and increased glutamic acid and pyruvate contents, and that these changes can be used as markers for evaluating the toxicity of nanoparticles. These markers can further be used to more closely evaluate the toxicity of nanoparticles.

The present invention also provides a method for evaluating the toxicity of nanoparticles, comprising the steps of: obtaining a tissue or cell sample from a mammal exposed to nanoparticles; analyzing the sample for glutamic acid content, pyruvate content, intracellular mitochondrial damage, a change in intracellular mitochondrial membrane potential, ROS (reactive oxygen species) content, and ATP content; and comparing the analysis result with that of a control group.

The present inventors have conducted studies to evaluate the toxic effect of exposure to nanoparticles by the change in cells or tissues caused by the nanoparticles, and as a result, have found that, when cells are treated with a specific or higher concentration of nanoparticles, the cells show changed glutamic acid concentration, increased ROS content, decreased ATP content, damaged intracellular mitochondrial inner membrane, changed intracellular mitochondrial membrane potential, and increased glutamic acid content and pyruvate content, and these changes can be used as independent markers for evaluating the toxicity of nanoparticles, thereby completing the present invention.

In one embodiment of the present invention, the nanoparticles may be any nanoparticles whose toxicity is increased upon reaction with biological tissue. More specifically, the nanoparticles include, but are not limited to, atmospheric nanoparticles, nanoparticles contained in cosmetic compositions, nanoparticles contained in pharmaceutical compositions, semiconductor nanoparticles, and the like.

The nanoparticles may have a core-shell structure wherein the shell may include silica, but the scope of the present invention is not limited thereto.

In one embodiment of the present invention, the method for evaluating the toxicity of nanoparticles may essentially comprise a step of analyzing the glutamic acid content or pyruvate content of cells.

In the method for evaluating the toxicity of nanoparticles according to the present invention, when the content of glutamic acid or pyruvate in cells is increased compared to that of the control group, the nanoparticles can be evaluated to have toxicity. The glutamic acid and pyruvate contents of cells can be measured by GS-MS analysis, but is not limited thereto.

The ROS content of cells can be measured by fluorescence analysis using 2',7'-dichlorodihydrofluorescin diacetate (DCFH-DA) staining, and the ATP content of cells can be measured by analyzing luminescence using an ATP assay system (Promega, USA), but the scope of the present invention is not limited thereto. When the ROS content is increased compared to that of the control group, the nanoparticles can be evaluated to have toxicity, and when the ATP content is increased compared to that of the control group, the nanoparticles can be evaluated to have toxicity.

In addition, the mitochondrial damage can be analyzed by an electron microscope.

Figure 8:
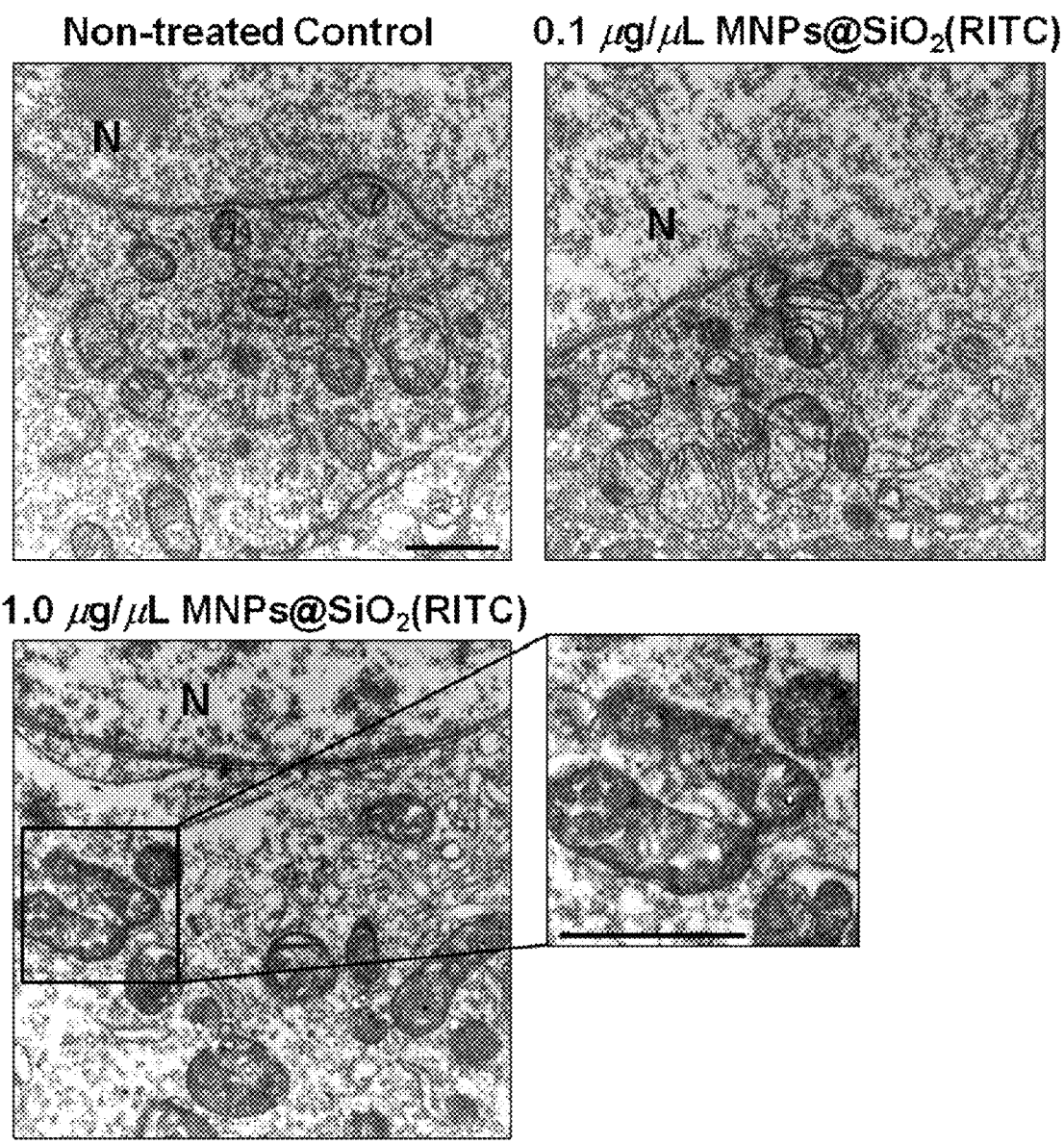
FIG. 8 is a set of transmission electron images of mitochondria in HEK 293 cells treated with MNPs@SiO$_2$ (RITC).

As can be seen in the Examples of the present invention and in FIG. 8, when the mitochondrial inner membrane structure is disintegrated, the nanoparticles can be evaluated to have toxicity.

Figure 11:
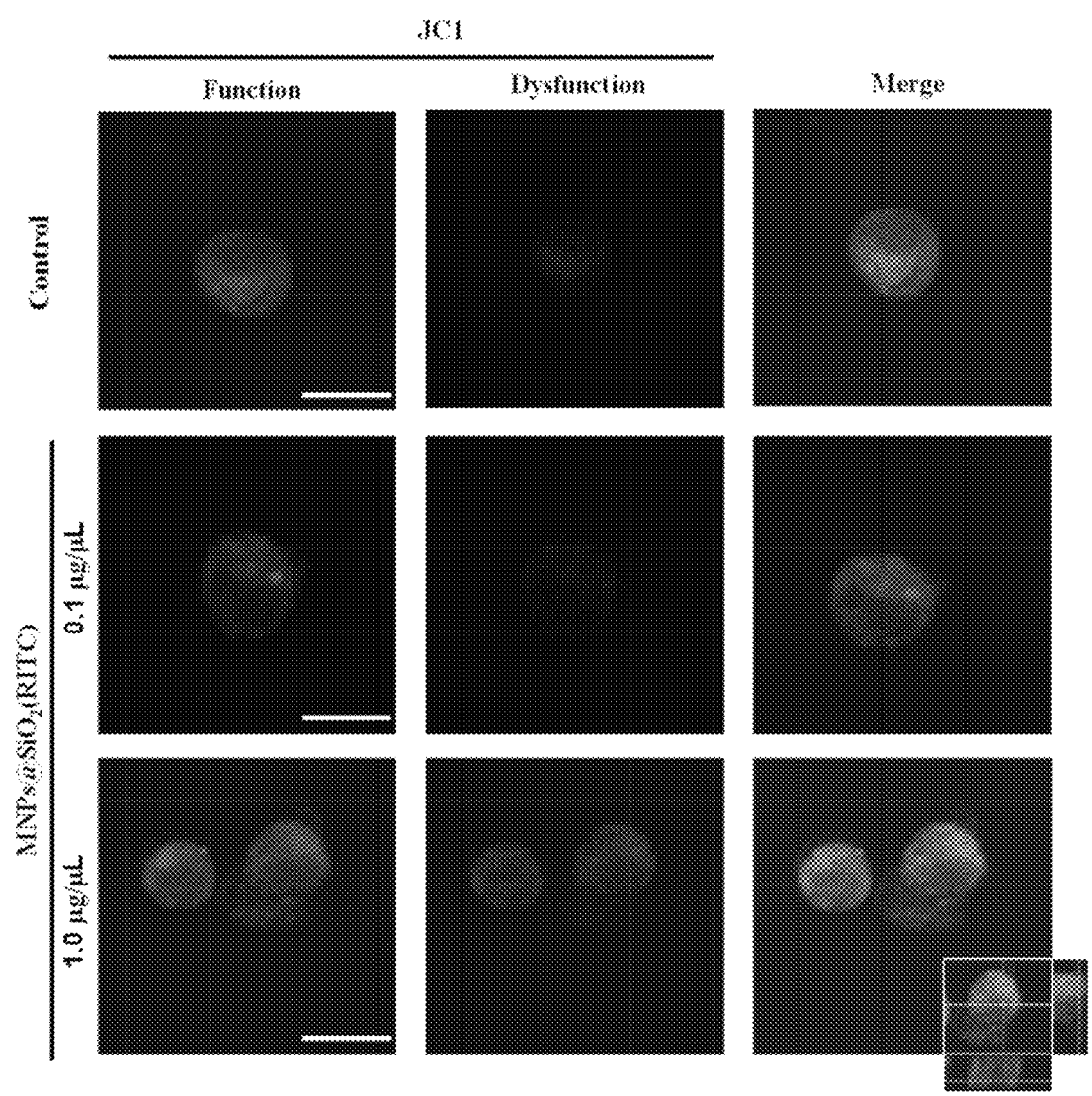
FIG. 11 shows the results of JC-1 staining showing the change in mitochondrial membrane potential caused by treatment with nanoparticles.

A change in mitochondrial membrane potential can be analyzed by staining cells with JC-1 reagent, and as shown in FIG. 11, when the mitochondrial membrane potential is changed compared to that of the control group, the nanoparticles can be evaluated to have toxicity.

Hereinafter, the present invention will be described in further detail with reference to examples. It is to be understood, however, that these examples are for illustrative purposes only and are not intended to limit the scope of the present invention. The examples of the present invention are provided in order to more completely explain the present invention to those skilled in the art.

Test Examples

The following test examples are those that are commonly applied to examples of the present invention.

1. Cell Culture and MNPs@SiO$_2$(RITC) Treatment

Human embryo kidney 293 (HEK 293) cells were used to evaluate the cytotoxicity of MNPs@SiO$_2$(RITC) because this cell line has been well characterized for its relevance to silica nanoparticle-induced cytotoxicity and the eventual renal toxicity models in humans. Cells were cultured in high-glucose Dulbecco's modified Eagle's medium (DMEM, Gibco, USA) containing 10% fetal bovine serum (FBS, Gibco, USA), 100 units/mL penicillin, and 100 µg/mL streptomycin (Gibco, USA). Cells were incubated at 37° C. in a 5% humidified CO$_2$ atmosphere. Media were removed and replaced every 3 days. MNPs@SiO$_2$(RITC) particles having a diameter of 50 nm were added directly to serum- and antibiotic-free culture medium. HEK 293 cells were seeded at a concentration of 2×10$^6$ cells/100 mm dish and incubated in 10 mL of medium containing various concentrations of MNPs@SiO$_2$(RITC) for 12 hours. Cells were then washed twice in phosphate buffered saline (PBS) and harvested using 0.25% trypsin/0.1% EDTA (Sigma, USA).

2. Fluorescence-Activated Cell Sorting (FACS) Analysis

For cell death assays, FACS analysis was performed using an Annexin V-FITC apoptosis detection kit (Becton Dickinson Biosciences, USA).

Briefly, cells harvested after culture were washed twice with cold PBS, after which they were resuspended in 100 µL of 1× binding buffer (10 mM Hepes, pH 7.4, 140 mM sodium chloride, and 2.5 mM calcium chloride). Then, 5 µL of Annexin V-FITC and propidium iodide (PI) was added to the samples, which were incubated for 15 min at 25° C. in dark conditions. To stop the reaction, 400 µL of 1× binding buffer was added to each tube. Cells were assayed by FACS (Becton Dickinson Facsvantage, USA), and data analysis was performed with Win MDI Version 2.9 (The Scripps Research Institute, USA).

3. Confocal Laser Scanning Microscopy (LSM) and Image Processing

MNPs@SiO$_2$(RITC)-treated HEK 293 cells were fixed in 4% paraformaldehyde solution, dehydrated, and mounted using anti-fade solution (R&D, USA). Cells were also stained with 4',6-diamidino-2-phenylindole (DAPI) for detection of the nuclei. Fluorescence images were acquired by confocal LSM (Olympus, Japan). DAPI and MNPs@SiO$_2$(RITC) were excited at 205 nm and 530 nm wavelength, respectively. Digital images were analyzed using LSM software (Leica, USA).

4. RNA Purification with RNAzol B

RNA was isolated from MNPs@SiO$_2$(RITC)-treated or nontreated HEK 293 cells using RNAzol B (Tel-Test, Inc., USA) and then purified using RNeasy Mini Kits (Qiagen, USA). Briefly, harvested cells were treated with 1 mL of RNAzol B. Chloroform was added, and then the cells were incubated at 4° C. for 5 min. Total RNA was precipitated with 600 µL of isopropyl alcohol, and RNA pellets were washed with 70% ethanol. RNA was eluted from the pellets using RNase-free water (WelGene, South Korea) and quantified by spectrophotometry (Eppendorf, USA) and agarose gel electrophoresis. The purity of the RNA used in the microarray and PCR experiments ranged from 1.9 to 2.0, based on the ratio of optical densities (OD) at 260/230 and 260/280.

5. Quantitative Reverse Transcription PCR (RT-PCR) and Real-Time PCR

To quantify expression of genes, total RNA samples were reverse-transcribed using the ImProm-II reverse transcription system (Promega, USA) and amplified using gene-specific primer pairs. Amplified PCR products were separated on 1% agarose gels and stained with ethidium bromide. The amounts of the amplified PCR products were calculated using Multi Gauge 3.0 software (Fujifilm, Japan) The expression levels of glutamic acid-related genes were determined using the RealMOD™ SYBR Green real-time PCR kit (iNtRON Biotechnology, Seongnam, South Korea) and DNA Engine (Bio-Rad, Hercules, Calif.), with gene-specific primer pairs. The reactions were carried out at 5° C. for 2 min and 95° C. for 30 sec, followed by 40 cycles of 95° C. for 5 sec and 57° C. for 30 sec. The PCR products were analyzed by generating a melting curve using MJ Opticon Monitor Version 3.1 (Bio-Rad, Hercules, Calif.).

6. Microarray Experiments and Data Analysis

For construction of the gene expression profile, total RNA was hybridized to a microarray gene chip (Affymetrix, USA). Briefly, the Affymetrix system (Beyond Bioinformatics ISTECH AATC) Human U133 Plus 2.0 50 K microarray, which contained 54 675 gene-specific probes, was used. Hybridization was performed overnight using 15 g of labeled RNA product. After hybridization, these arrays were washed several times and scanned using Affymetrix scanners. Pretreatment was performed using GCOS, global scaling in GenPlex 3.0 software (ISTECH, South Korea). Gene expression differences were confirmed using MA plot with control cells and experimental arrays. The actions of genes whose expression changed more than 2-fold were examined by Ingenuity Pathway Analysis (IPA version 8.5, Ingenuity Systems).

7. Sample Preparation for AA Profiling Analysis in Cells

AAs in nontreated HEK 293 cells (control group) and HEK 293 cells treated with MNPs (treated group) at concentrations of 0.1 and 1.0 µg/µL were identified by GC-MS. Briefly, aliquots of each group ($1 \times 10^5$ cells) were adjusted to pH 12 after addition of IS (International Standard, norvaline, 200 ng). A two-phase EOC reaction was performed in the aqueous phase by vortexing for 5 min with ECF (ethyl chloroformate, 20 µL) in the dichloromethane phase (1 mL). The reaction mixture was sequentially extracted with diethyl ether (3.0 mL) and ethyl acetate (2.0 mL), which were evaporated to dryness under nitrogen reflux (40° C. The residue was reacted (60° C. for 30 min) with MTBSTFA (20 µL) in toluene (20 µL) for GC-SIM-MS.

8. Gas Chromatography-Mass Spectrometry

GC-MS analysis was were performed using an Agilent 6890 gas chromatograph, interfaced with an Agilent 5973 mass-selective detector (70 eV, electron impact mode) and installed with an Ultra-2 (5% phenyl-95% methylpolysiloxane bonded phase; 25 m×0.20 mm i.d., 0.11 µm film thickness) cross-linked capillary column (Agilent Technologies, USA). The temperatures of the injector, the interface and the ion source were 260, 300, and 230° C., respectively. Helium was used as a carrier gas at a flow rate of 0.5 mL/min with constant flow mode. Samples were introduced in the splitinjection mode (10:1). The temperature for AA (amino acid) analysis was initially set at 140° C. (2 min) and increased first to 240° C. at 5° C./min and then to 300° C. (3 min) at 30° C./min. The temperature for OA (organic acid) analysis was initially set at 100° C. (2 min) and increased first to 250° C. at 5° C./min and then to 300° C. (5 min) at 20° C./min. The mass range scanned was 50-600 u at a rate of 0.99 scans/sec. In the SIM mode, three characteristic ions for each AA were used for peak identification and quantification.

9. Transmission Electron Microscopic Observation

Cells were harvested using trypsin/EDTA and washed twice with PBS. The cells were then fixed with Karnovsky's fixative solution (1% paraformaldehyde, 2% glutaraldehyde, and 2 mM calcium chloride) for 48 hours and washed with cacodylate buffer. Then, the cells were incubated in 1% osmium tetroxide ($OsO_4$) solution containing 0.05% potassium ferrocyanide ($K_4Fe(CN)_6$) for 90 min. Subsequently, the cells were sectioned using Reichert Jung Ultracul S (Leica, USA). After the cells were stained with uranyl acetate and lead citrate, they were observed and photographed under TEM (JEM-1400, JEOL Ltd., Japan). Images were obtained at 25 000× magnification in randomly chosen fields from several samples.

10. Measurement of Reactive Oxygen Species (ROS)

The level of intracellular ROS was evaluated by 2',7'-dichlorodihydrofluorescein diacetate (DCFH-DA) dye. Briefly, $1 \times 10^4$ and $2 \times 10^4$ cells were seeded in chamber slides and a black 96-well plate, respectively, and treated with MNPs@SiO$_2$(RITC) (0.1 and 1.0 µg/µL) for 12 hours. After the medium was removed, the cells were washed twice with PBS. Then, 1×DCFH-DA/medium solution was added to each well, and the cells were incubated at 37° C. for 1 hour. These samples were washed twice with PBS, and fluorescence was measured using confocal LSM (Olympus, Japan) and Gemini EM fluorescence microplate reader (Molecular Devices, USA) at 480 nm excitation/530 nm emission. For detection of nuclei with confocal LSM, the cells were stained with DAPI.

11. Measurement of Adenosine Triphosphate (ATP) Concentration

The ATP concentration of cells was measured using an ATP assay system (Promega, USA). Briefly, cells were harvested using 0.25% trypsin/0.1% EDTA and washed twice with PBS. The harvested cells were resuspended in 0.1% trichloroacetic acid (TCA, Sigma, USA) solution and incubated at room temperature for 10-30 min. Luciferin reagent was mixed with reconstitution buffer solution. The resuspended samples were treated with 50 µL of the luciferin reagent/buffer mixture and then split in 96-well cell culture plates. After 10 min of incubation at 25° C., the luminescence of each well was measured with LMaxII$^{384}$ (MDS Analytical Technologies, USA), and images were obtained using LAS-1000 (FUGIFILM, Japan).

Example 1: Evaluation of Cytotoxicity of MNPs@SiO$_2$(RITC)

To evaluate the cytotoxicity of MNPs@SiO$_2$(RITC), HEK 293 cells were treated with 0.01, 0.1 and 1.0 µg/µL of MNPs@SiO$_2$(RITC) for 12 hours, and the observation of morphological change of the cells was performed. In the cells treated with these concentration of MNPs@SiO$_2$(RITC), morphological changes, such as membrane or organelle destruction were not observed (see FIG. 1A). To determine the viability in response to treatment with two different concentrations of MNPs@SiO$_2$(RITC) (0.1 and 1.0 µg/µL), the samples were labeled with Annexin V and PI and analyzed by a fluorescence-activated cell sorter (FACS). The results of the analysis are shown in FIGS. 1B and 1C. The viability of cells was preserved at 99.34 and 98.69% for 0.1 and 1.0 µg/µL concentrations of MNPs@SiO$_2$(RITC), respectively. Compared to the nontreated control, FACS analysis showed no significant changes in the viability of the MNPs@SiO$_2$(RITC)-treated cells. Furthermore, when MTS assays were conducted to assess the cytotoxicity of MNPs@SiO$_2$(RITC) after 3 or 7 days of treatment with 0.01 or 1.0 µg/µL, no significant cytotoxicity was observed compared with the nontreated control. These results suggest that treatment with MNPs@SiO$_2$(RITC) does not influence the viability of HEK 293 cells, and thus cell growth and apoptosis are not influenced by these concentrations of MNPs@SiO$_2$(RITC) (0.1 and 1.0 µg/µL).

Figure 2:
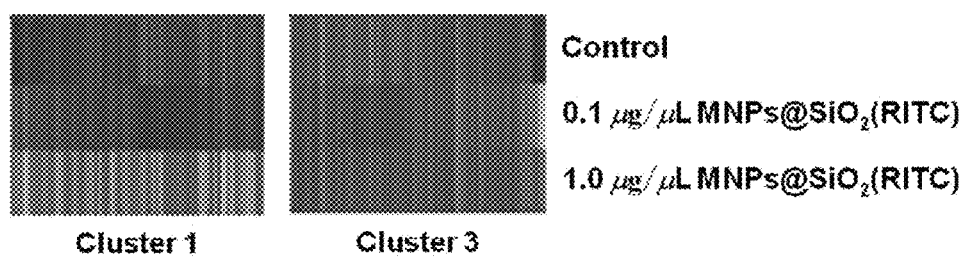
FIG. 2 shows the results of analyzing the change in gene expression of HEK 293 cells treated with MNPs@SiO$_2$ (RITC).
Figure 2:
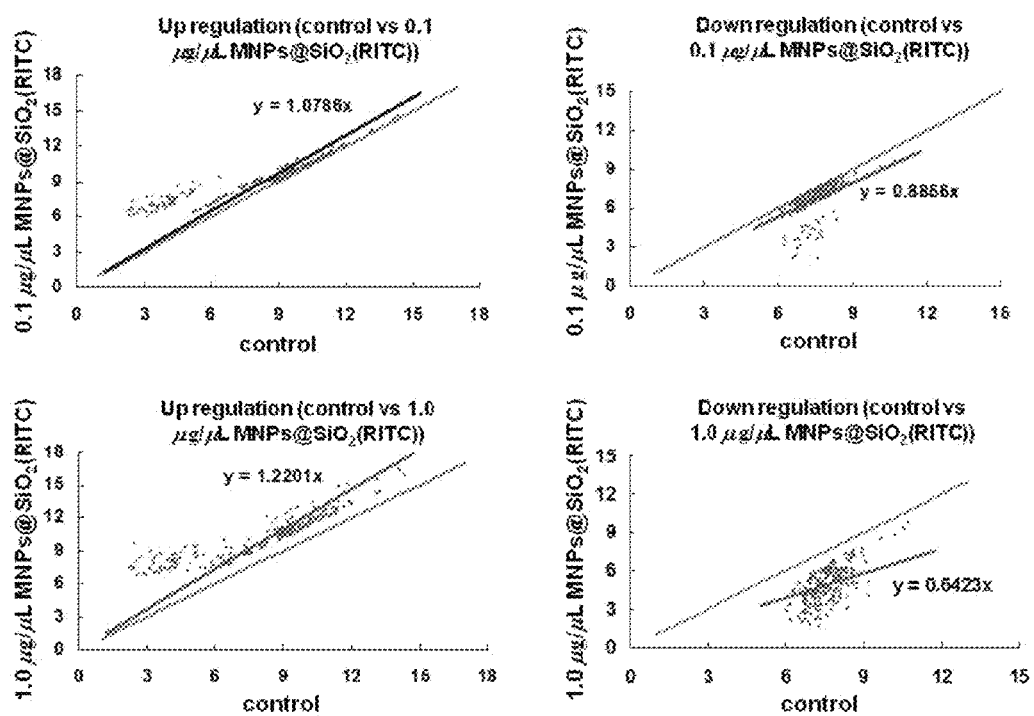

Example 2: Gene Expression and AA Composition Profiling in MNPs@SiO$_2$(RITC)-Treated HEK 293 Cells For identification of genes upregulated and downregulated in MNPs@SiO$_2$(RITC)-treated HEK 293 cells, gene expression analysis was performed on HEK 293 cells treated with 0, 0.1 and 1.0 µg/µL of MNPs@SiO₂(RITC) using oligonucleotide microarrays. After normalization of gene expression, 5,966 functional gene probes were classified into eight clusters using GenPlex 2.0 software. Because clusters 1 and 3 showed significant signal changes, they were examined in further detail. Of the 466 genes in these clusters, 291 genes were either up- or down-regulated at a MNPs@SiO₂ (RITC) concentration of 1.0 µg/µL, using a 1.25-fold expressional change as a cutoff (see FIG. 2A). The signal intensities of total functional genes belonging to clusters 1 and 3 were plotted according to comparison between intensity levels of groups and then a comparison-plot pattern could be separated into high and low differential expression (see FIG. 2B). Expressional difference between MNPs@SiO₂(RITC)-treated cells and nontreated cells was related to the concentration of MNPs@SiO₂(RITC). When 0.1 µg/µL MNPs@SiO₂(RITC)-treated cells were compared to the nontreated control, 7.8% of genes were upregulated and 1.4% were downregulated. However, in cells treated with 1.0 µg/µL of MNPs@SiO₂(RITC), 22.0% of genes were upregulated and 35.8% were downregulated. The present inventors categorized genes whose expression significantly changed expression after 1.0 µg/µL MNPs@SiO₂(RITC) treatment, but did not significantly change after 0.1 µg/µL MNPs@SiO₂(RITC) treatment. Table 1 below lists the functional categories of the 291 genes, including 205 upregulated and 86 downregulated genes after treatment with high concentrations (1.0 µg/µL) of MNPs@SiO₂(RITC).

TABLE 1

| Biological Processing | Up regulation | Down regulation |
|---|---|---|
| DNA related gene | | |
| DNA replication and processing | 6 | n.c.* |
| DNA repair | 3 | 1 |
| Transcription processing | | |
| RNA polymerase II | 9 | 3 |
| Regulation of transcription from RNA polymerase II | 8 | 2 |
| Transcription | 14 | 4 |
| Regulation of transcription | 3 | 2 |
| Apoptosis | 4 | n.c. |
| Transport | | |
| Cation, electron and ion transport | 12 | 11 |
| Protein transport | 7 | 1 |
| Material transport | 6 | 6 |
| Cell adhesion, motability and cytoskeleton | | |
| Cell adhesion and movement | 17 | 6 |
| Cell cytoskeleton | 7 | n.c. |

TABLE 1-continued

| Biological Processing | Up regulation | Down regulation |
|---|---|---|
| Signal | | |
| Intracellular signaling | 8 | 1 |
| Cell to cell signaling | 3 | 2 |
| Pathway and genesis signaling | 11 | 14 |
| Protein process | 17 | 6 |
| Ubiquitin relation | 18 | 2 |
| Cell cycle, growth, development and aging | | |
| Proliferation, differentiation and development | 6 | 1 |
| Cell cycle | 7 | 3 |
| Cell growth and aging | 5 | n.c. |
| Proliferation, differentiation and development | 9 | 8 |
| Cell metabolism | 17 | 6 |

*n.c.: no changed

As can be seen in Table 1 above, the expression of metabolism-related genes was downregulated due to treatment with MNPs@SiO₂(RITC) Thus, the present inventors performed AA profiling analysis. The compositions of seven AAs from nontreated control and 0.1 µg/µL and 1.0 µg/µL MNPs@SiO₂(RITC)-treated cells are shown in Table 2 below, and the values that were normalized to the mean level of the corresponding control group are shown in FIG. 3.

TABLE 2

| | | | Composition$^a$ | | | Normalized value$^e$ | |
|---|---|---|---|---|---|---|---|
| | | | | MNPs@SiO₂(RITC) treated group (n = 3) | | | |
| No. | Amino acid | Control (n = 3) | Low conc. (0.1 µg/µL) | High conc. (1.0 µg/µL) | P value$^d$ | Low conc. | High conc. |
| 1 | Alanine | 11.7 ± 0.2 | 9.6 ± 0.5 (0.001)$^b$ | 9.9 ± <0.1 (0.00004)$^c$ | 0.2 | 0.8 | 0.8 |
| 2 | Valine | 9.2 ± 0.1 | 8.6 ± 0.2 (0.002) | 6.4 ± 0.3 (0.00003) | 0.0001 | 0.9 | 0.7 |
| 3 | Leucine | 15.8 ± 0.1 | 15.7 ± 0.7 (0.4) | 11.7 ± 0.7 (0.0003) | 0.001 | 1.0 | 0.7 |
| 4 | Isoleucine | 13.5 ± 0.1 | 12.4 ± 0.7 (0.03) | 9.1 ± 0.6 (0.0001) | 0.001 | 0.9 | 0.7 |
| 5 | Proline | 6.1 ± 0.2 | 6.6 ± 0.3 (0.04) | 4.8 ± 0.1 (0.0006) | 0.0004 | 1.1 | 0.8 |
| 6 | Glutamic acid | 19.0 ± 0.9 | 20.5 ± 1.6 (0.1) | 37.5 ± 2.6 (0.0001) | 0.0003 | 1.1 | 2.0 |
| 7 | Tyrosine | 24.8 ± 0.9 | 26.6 ± 0.5 (0.02) | 20.7 ± 0.9 (0.002) | 0.0002 | 1.1 | 0.8 |

Figure 3:
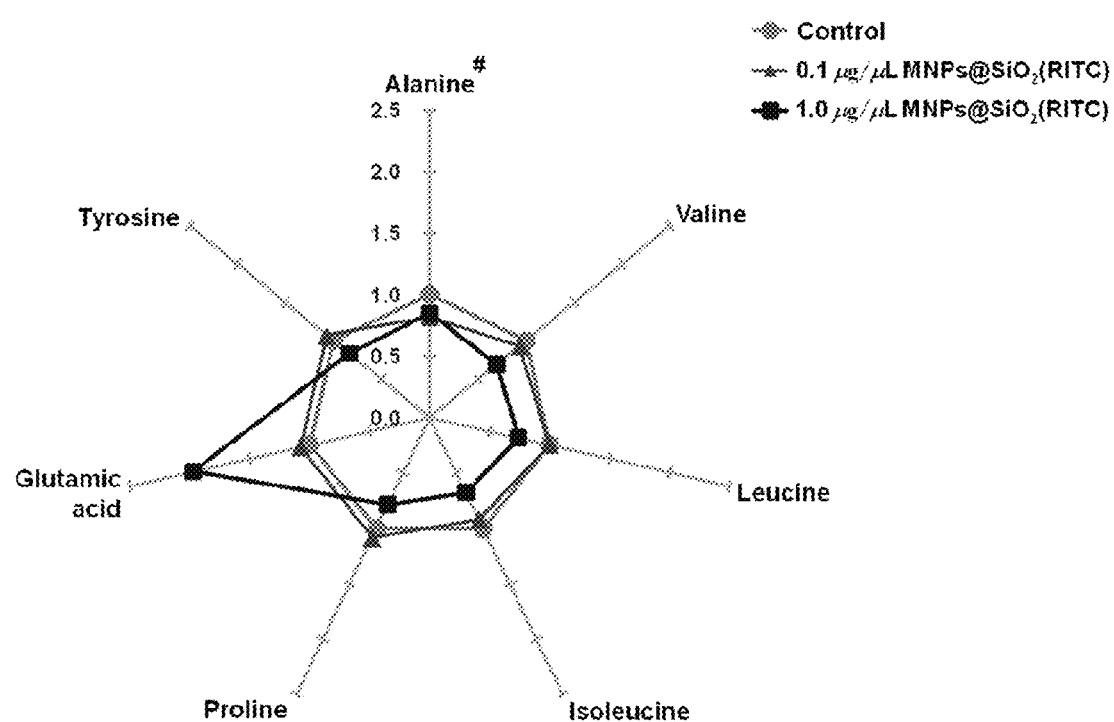
FIG. 3 shows the composition levels of amino acids in HEK 293 cells treated with MNPs@SiO$_2$(RITC).
Figure 4:
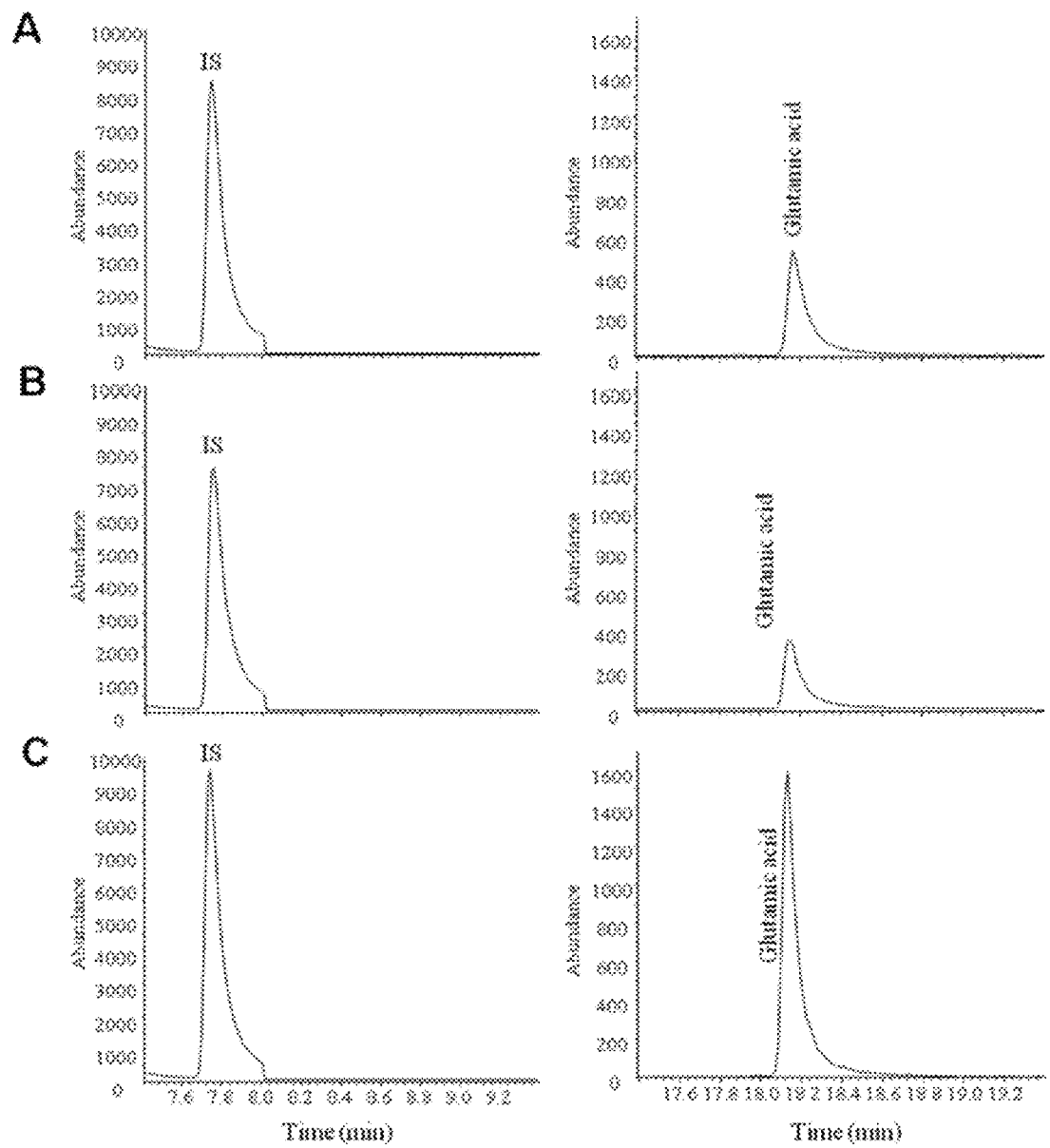
FIG. 4 shows selected ion monitoring (SIM) chromatograms of HEK 293 cells treated with MNPs@SiO$_2$(RITC).

As can be seen in Table 2 above and FIG. 3, the group treated with 1.0 µg/µl of MNPs@SiO₂(RITC) showed a marked increase in the expression of glutamic acid (about 200%) and a reduction (≤30%) of other amino acids (alanine, valine, leucine, isoleucine, proline, and tyrosine). On the other hand, the group treated with 0.1 µg/µL of MNPs@SiO₂(RITC) showed slight changes (elevation or reduction, ≤20%) by comparison with those of the control group. Selected ion monitoring (SIM) chromatograms also revealed that the expression of glutamic acid was significantly increased in the 1.0 µg/µL MNPs@SiO₂ (RITC)-treated cells (see FIG. 4). As can be seen in FIG. 4, the relative peak area ratio of glutamic acid to that of the internal standard (IS) was 0.056 (FIG. 4A; control), 0.045 (FIG. 4B; the group treated with 0.1 µg/µL of MNPs@SiO₂(RITC)), and 0.173 (FIG. 4C; the group treated with 1.0 µg/µL of MNPs@SiO₂(RITC)). In particular, glutamic acid levels in the group treated with 1.0 µg/µL of MNPs@SiO₂(RITC) were much higher than those of the control group and the group treated with 0.1 µg/µL of MNPs@SiO₂(RITC).

The branched-chain amino acids (BCAAs, such as valine, leucine, and isoleucine) play essential roles as stimulators of the immune system and in the synthesis of glutamic acid; more than 30% of glutamic acids are derived from BCAAs through the BCAA transaminase pathway. As can be seen in Table 2 and FIG. 3, alteration of BCAAs between high concentration MNPs@SiO$_2$(RITC)-treated cells and the control group was also observed, suggesting that the amino acids influence the change in glutamic acid expression caused by MNPs@SiO$_2$(RITC).

Example 3: Ingenuity Pathway Analysis (IPA) of the Glutamic Acid Metabolic Network in High Concentration MNPs@SiO$_2$(RITC)-Treated Cells Since the GC-MS analysis results indicated that glutamic acid levels were elevated more than 2-fold in cells treated with 1.0 μg/μL of MNPs@SiO$_2$(RITC) compared to the control group, the present inventors constructed a genetic network of the glutamic acid metabolic pathway using Ingenuity pathway analysis (IPA) software to understand the interaction between genes.

The glutamic acid metabolic pathway was constructed on the basis of the metabolic correlation between genes whose expression was changed (fold change >1.25) due to treatment with 1.0 μg/μL of MNPs@SiO$_2$(RITC). The constructed glutamic acid metabolic pathway is shown in FIG. 5.

As can be seen in FIG. 5, genes, including aldehyde dehydrogenase 4 family member A1 (ALDH4A1), glutamic-pyruvate transaminase 2 (GPT2), glutamate dehydrogenase 1 (GLUD1), glutamicoxaloacetic transaminase 2 (GOT2), and glutamic acid decarboxylase 1 (GAD1), are involved in the glutamic acid metabolic pathway and are disturbed in cells treated with 1.0 μg/μL of MNPs@SiO$_2$(RITC). These results suggest that disturbance of glutamic acid in cells treated with high concentrations of MNPs@SiO$_2$(RITC) might be caused by expression confusion of various genes that are associated with the glutamic acid metabolic pathway.

Example 4: Analysis of Gene Expression Related to Glutamic Acid Metabolism by Semi-Quantitative PCR It was shown that genes that are involved in catalyzing the conversion of glutamic acid into other metabolic precursors or amino acids, such as GLUD1, GOT2, GAD1, and GLUL, were downregulated in cells treated with 1.0 μg/μL of MNPs@SiO$_2$(RITC) (see FIG. 6A). In particular, the expression of GLUD1 was about 47% lower than that of the nontreated control, and the expressions of GOT2, GLUL and GAD1 were 33, 25 and 61% lower than that of the nontreated control, respectively. However, cells treated with 0.1 μg/μL MNPs@SiO$_2$(RITC) did not show a significant change in gene expression compared to the control group.

Figure 6:
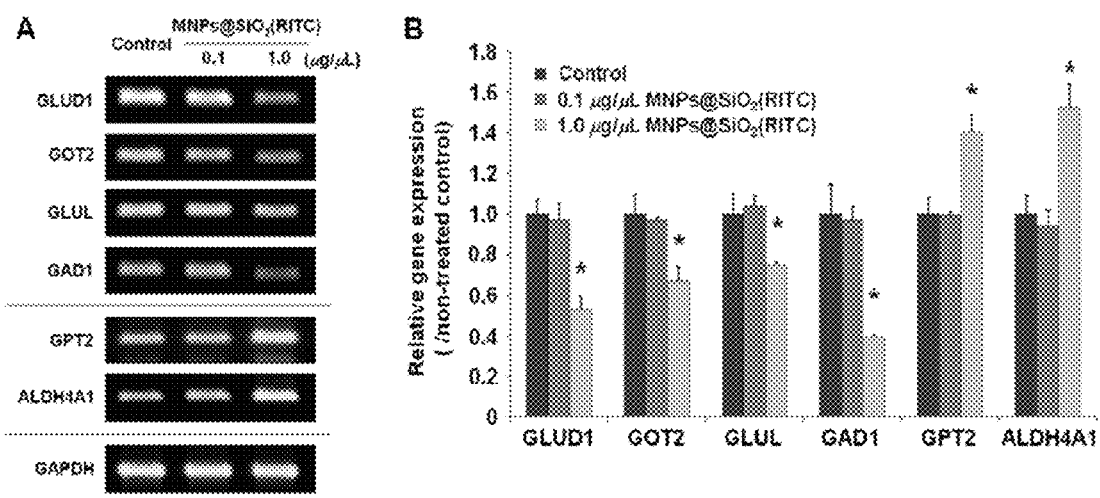
FIG. 6 shows the results of PCR showing the changes in gene expression in HEK 293 cells treated with MNPs@SiO$_2$ (RITC).

On the other hand, the expressions of GPT2 and ALDH4A1, known as genes which catalyze the conversion of the amino group of alanine and proline to glutamic acid, were shown to increase by about 41 and 53% in cells treated with 1.0 μg/μL MNPs@SiO$_2$(RITC), respectively (see FIG. 6B). These results are consistent with the GC-MS analysis results revealing that the cells treated with 1.0 μg/μL of MNPs@SiO$_2$(RITC) show decreases in the alanine and proline levels, but an increase in the glutamic acid level (see FIG. 3). These results suggest that alanine and proline may be converted to glutamic acid by overexpressed GPT2 and ALDH4A1 genes.

Figure 7:
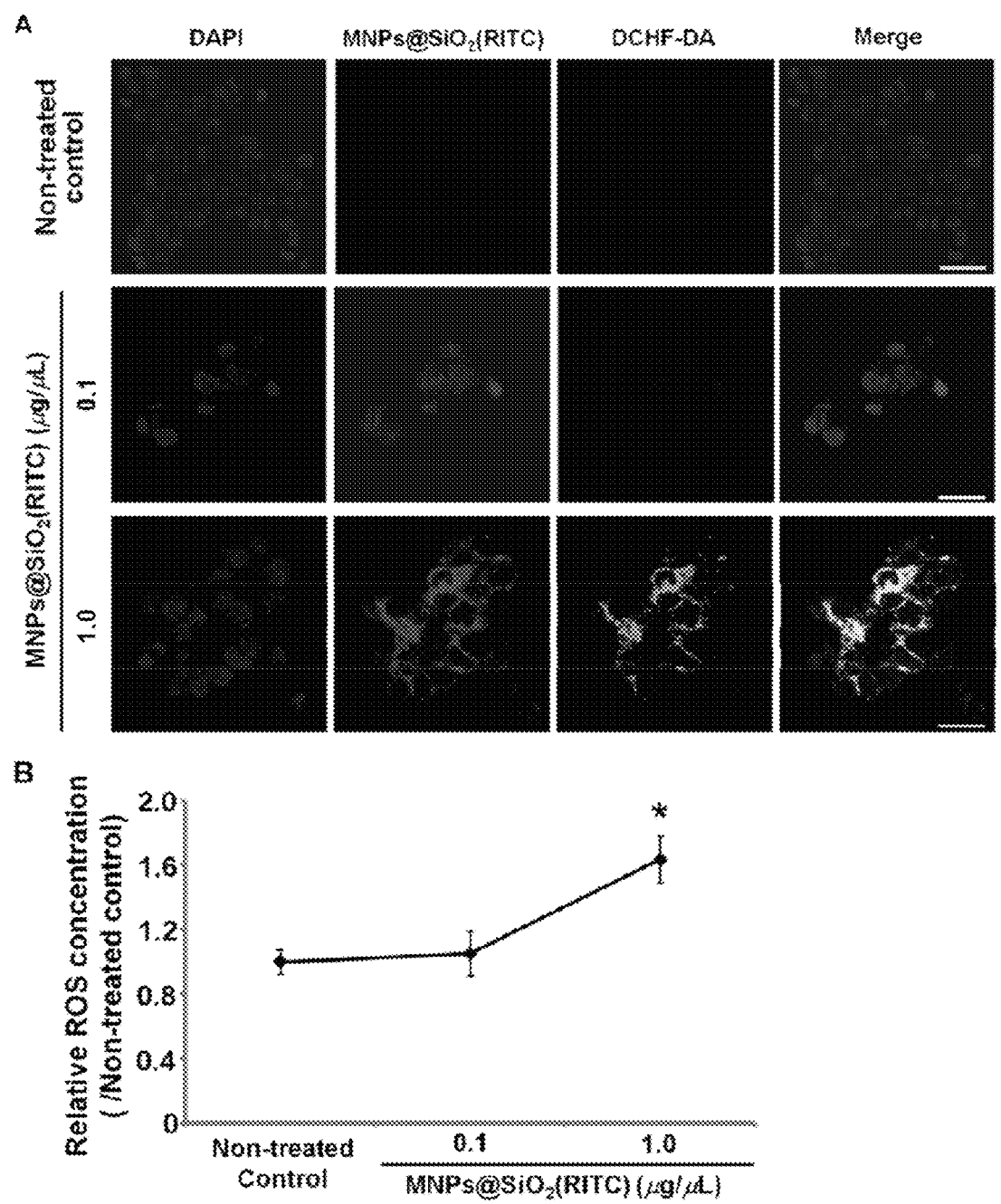
FIG. 7 shows the results of analyzing the ROS content of HEK 293 cells treated with MNPs@SiO$_2$(RITC).

Example 5: Analysis of Reactive Oxygen Species (ROS) Generation and Mitochondrial Damage Because several studies reported that nanoparticles induce oxidative stress, analysis was performed to determine whether MNPs cause oxidative stress and thus damage to mitochondria. 2',7'-Dichlorodihydrofluorescin diacetate (DCFH-DA) staining was conducted to determine the generation of intracellular ROS induced by MNPs@SiO$_2$(RITC). FIG. 7 shows the results of visualizing MNPs@SiO$_2$(RITC)-treated cells with confocal LSM.

As can be seen in FIG. 7A, the concentration of reactive oxygen species was increased in the group treated with 1.0 μg/μL MNPs@SiO$_2$(RITC) (FIG. 7A). The ROS concentration, which was quantified, was increased by about 63% compared to that in the control group (FIG. 7B). However, there was no difference in the ROS concentration between the control group and the group treated with 0.1 μg/μL of MNPs@SiO$_2$(RITC).

Example 6: Analysis of Alteration of ATP Synthesis and Composition of Organic Acids Related to Krebs Cycle FIG. 8 shows the results of analyzing ROS-induced mitochondrial damage with a transmission electron microscope (TEM) and a JC-1 assay kit (Molecular Probe, USA). As can be seen in FIG. 8, mitochondrial inner structures were disintegrated in cells treated with 1.0 μg/μL MNPs@SiO$_2$(RITC).

However, there was no difference in mitochondrial inner structures between the control group and the group treated with 0.1 μg/μL MNPs@SiO$_2$(RITC).

The major function of mitochondria is to produce adenosine triphosphate (ATP), which is a major energy source for cells, through the Krebs cycle, and it was predicted that ATP production would be changed by damaged mitochondria. Thus, ATP synthesis was measured with a luminescence-based ATP concentration assay system.

Figure 9:
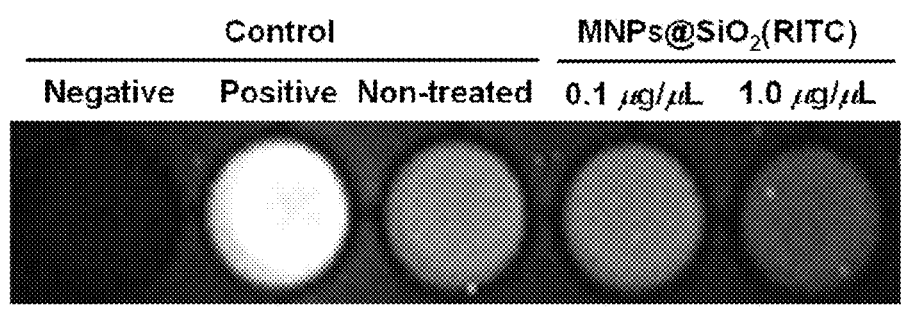
FIG. 9 shows the ATP concentration of HEK 293 cells treated with MNPs@SiO$_2$(RITC).
Figure 9:
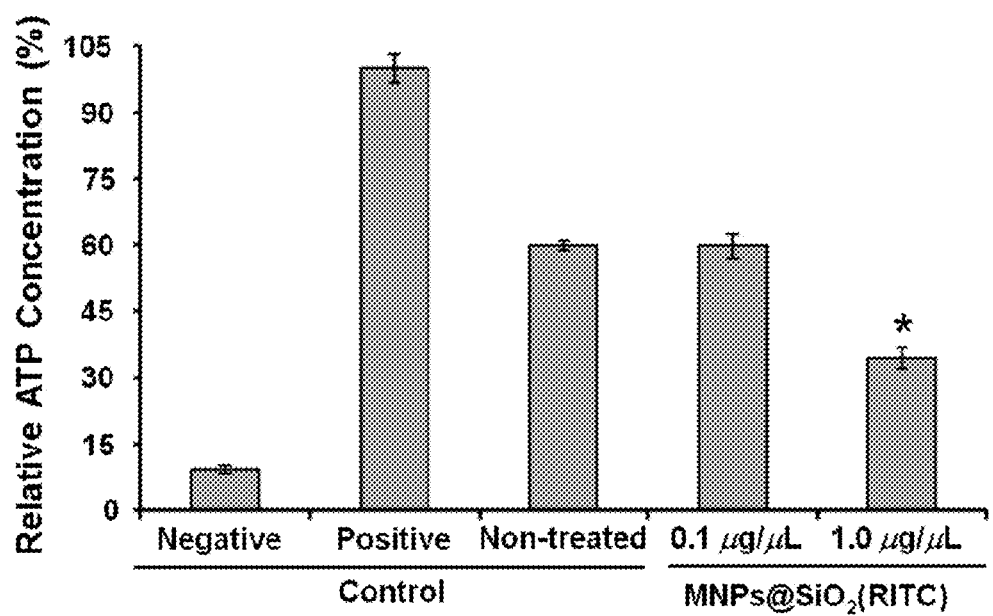

When 1.0 μg/μL MNPs@SiO$_2$(RITC)-treated cells were compared to a nontreated control, the ATP concentration was decreased, whereas 0.1 μg/μL MNPs@SiO$_2$(RITC)-treated cells showed no significant difference compared to the nontreated control (see FIG. 9A). In addition, the ATP concentration, which was quantitatively evaluated by luminescence images, showed a reduction of approximately 50% in 1.0 μg/μL MNPs@SiO$_2$(RITC)-treated cells versus the nontreated control (see FIG. 9B). These results suggest that ATP production was reduced by mitochondria damaged by treatment with 1.0 μg/μL MNPs@SiO$_2$(RITC).

Figure 10:
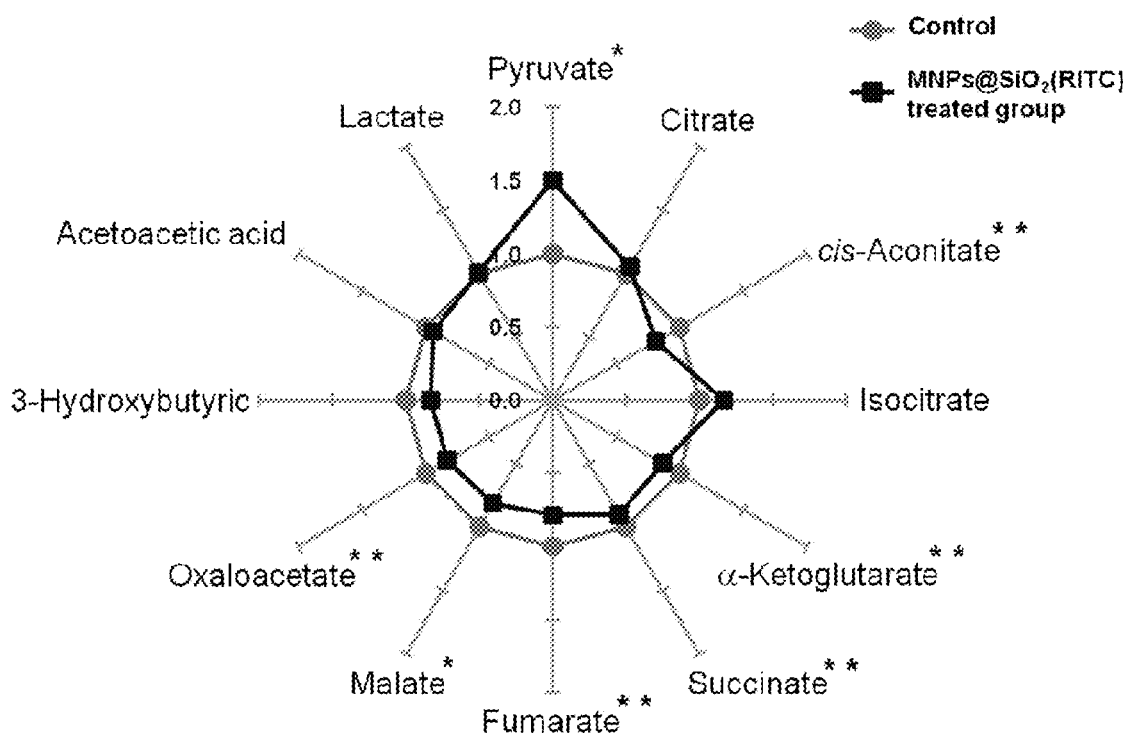
FIG. 10 shows the results of analyzing the composition levels of organic acids (OAs) in the Krebs cycle in MNPs@SiO$_2$(RITC)-treated HEK 293 cells by GC-MS.

It is known that a significant portion of cellular ATP is produced through the Krebs cycle in mitochondria and that the Krebs cycle is the complex metabolic process of organic acids such as pyruvate, α-ketoglutarate and oxaloacetate. Because a decrease in ATP means the abnormal activity of the Krebs cycle, a change in the composition of organic acids (OAs) was analyzed by GC-MS. The results of the analysis are shown in FIG. 10. As can be seen in FIG. 10, the expression of pyruvate in the MNPs@-SiO$_2$(RITC)-treated group was elevated by more than 50%, the expressions of α-ketoglutarate and oxaloacetate, which play an important role in the Krebs cycle, were reduced by 17% and 14%, respectively. In addition, other organic acids in the Krebs cycle, such as fumarate and malate, were also decreased in cells treated with 1.0 μg/μL of MNPs@SiO$_2$(RITC).

Example 7: Analysis of Alteration of Mitochondrial Membrane Potential

The mitochondrial membrane functions to allow mitochondria to perform its original function while maintaining a constant potential.

The change in the mitochondrial membrane potential is used as a marker for evaluating whether mitochondria normally function. Thus, the present inventors analyzed whether mitochondria normally function, using a JC-1 assay kit (Molecular Probe, USA) that enables determination of a change in the mitochondrial membrane potential.

The results of the analysis are shown in FIG. 11. As can be seen in FIG. 11, the mitochondrial membrane potential in the group treated with 0.1 μg/μL of MNPs@SiO$_2$(RITC) was similar to that in the control group, but the mitochondrial membrane potential in the group treated with 0.1 μg/μL of MNPs@SiO$_2$(RITC) significantly changed compared to that in the control group. This suggests that the mitochondrial membrane potential changes upon treatment with a high concentration of nanoparticles so that mitochondria cannot normally perform their original function.

Figure 12:
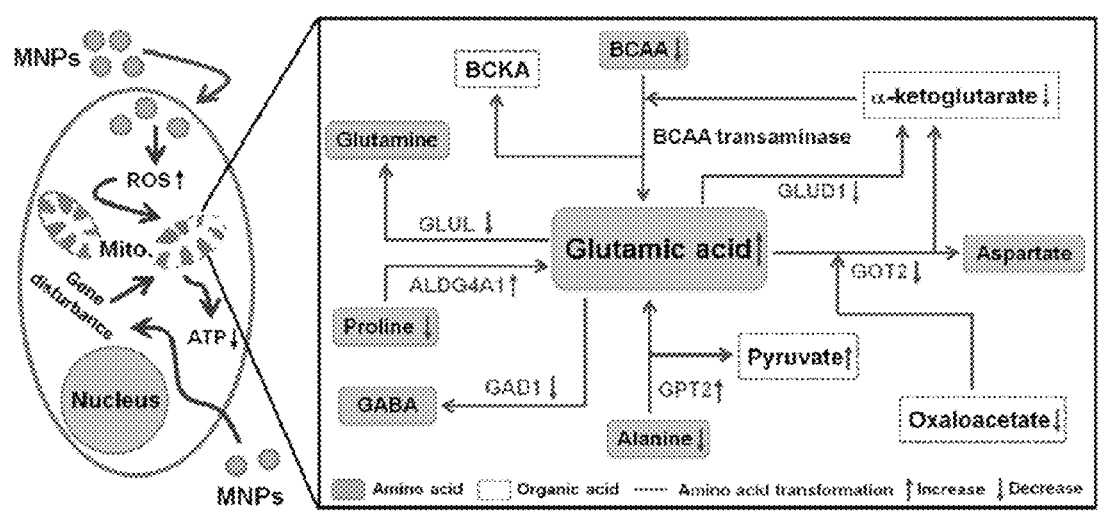
FIG. 12 is a schematic diagram showing the change in intracellular mechanism caused by treatment with nanoparticles.

Considering the above results together, it can be seen that, when cells are treated with a high concentration (1.0 μg/μL) of nanoparticles, the change in gene expression in the cells can be induced, and particularly, the expression of metabolism-related genes in the cells can be significantly changed. This induces a change in metabolites and results in a significant change in glutamate. In addition, it was found that reactive oxygen species induced by a high concentration of nanoparticles cause mitochondrial damage which leads to a change in mitochondrial membrane potential and a decrease in ATP synthesis, and the reactive oxygen species can also change the composition of organic acids related to the Krebs cycle. However, when cells are treated with a low concentration of MNPs, results similar to those of a non-treated control group are shown and the genes and metabolites in the cells are not significantly changed. These mechanisms are summarized in FIG. 12.

Thus, a high concentration of nanoparticles can affect genes and metabolites in the body. A clear methodological guide or biological marker for evaluating the safety of nanoparticles has not yet been standardized, but the present invention provides a method capable of clearly evaluating the safety of nanoparticles.

As described above, the biomarker according to the present invention is a gene marker having a high correlation with the toxicity of nanoparticles, and the use of the biomarker can determine whether nanoparticles have toxicity, with high detection sensitivity.

In addition, the method for evaluating the toxicity of nanoparticles according to the present invention can be useful in monitoring or evaluating the toxicity of nanoparticles by analyzing factors having a high correlation with the toxicity of nanoparticles. Furthermore, the method of the present invention can be effectively used as a tool for studying various diseases caused by exposure to nanoparticles or evaluating the effects of nanoparticles on health.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for determining a risk of toxicity of MNPs@SiO$_2$ nanoparticles, comprising the steps of:
   culturing HEK 293 cells;
   treating the cultured cells with the nanoparticles;
   detecting mRNA gene expression of aldehyde dehydrogenase 4 family member A1 (ALDH4A1), glutamic-pyruvate transaminase 2 (GPT2), glutamate dehydrogenase 1 (GLUD1), glutamicoxaloacetic transaminase 2 (GOT2), glutamic acid decarboxylase 1 (GAD1), and glutamate-ammonia ligase (GLUL) of the treated cells;
   comparing the mRNA gene expression between the treated cells and non-treated cells; and
   determining the risk of the toxicity if,
      a gene expression level of the ALDH4A1 in the treated cells increases 1.25-fold or more than the non-treated cells, and
      the gene expression level of the GPT2, GLUD1, GOT2, GAD1, and GLUL in the treated cells decreases 0.75-fold or less than the non-treated cells.

2. The method of claim 1, wherein the method further comprises the steps of:
   detecting at least one selected from the group consisting of reactive oxygen species (ROS) content, ATP content, intracellular mitochondrial damage, a change in intracellular mitochondrial membrane potential, glutamic acid content, and pyruvate content from the treated cells;
   comparing the detected result with the non-treated cells; and
   determining the risk of the toxicity if,
      the glutamic acid, the pyruvate content, the ROS contents are more increased than the non-treated cells, or
      the intracellular mitochondrial damage, the change in intracellular mitochondrial membrane potential, and the ATP content are decreased than the non-treated cells.

3. A method for determining a risk of toxicity of MNPs@SiO$_2$ nanoparticles, comprising the steps of:
   culturing HEK 293 cells;
   treating the cultured cells with the nanoparticles;
   detecting at least one selected from the group consisting of glutamic acid content, pyruvate content, intracellular mitochondrial damage, a change in intracellular mitochondrial membrane potential, reactive oxygen species (ROS) content, and ATP content from the treated cells;
   comparing the detected result with non-treated cells; and
   determining the risk of the toxicity if,
      the glutamic acid, the pyruvate content, the ROS contents are more increased than the non-treated cells, or
      the intracellular mitochondrial damage, the change in intracellular mitochondrial membrane potential, and the ATP content are decreased than the non-treated cells.

4. The method of claim 3, wherein the nanoparticles are atmospheric nanoparticles, nanoparticles contained in cosmetic compositions, nanoparticles contained in pharmaceutical compositions, or semiconductor nanoparticles.

5. The method of claim 3, wherein the ATP content is decreased by exposure to the nanoparticles.

6. The method of claim 3, wherein the ROS content, the glutamic acid content and the pyruvate content are increased by exposure to the nanoparticles.

* * * * *